United States Patent
Graham

(10) Patent No.: US 12,257,357 B2
(45) Date of Patent: Mar. 25, 2025

(54) APPARATUS AND METHOD FOR MODIFYING A SPRAYER BOTTLE INTO AN OZONATING AND IONIZING WATER SPRAYER BOTTLE AND FOR PROVIDING HUMIDIFICATION WITH OZONATED AND IONIZED WATER

(71) Applicant: Professional Server Certification Corporation, Madison, SD (US)

(72) Inventor: Robert V. Graham, Wentworth, SD (US)

(73) Assignee: Professional Server Certification Corporation, Madison, SD (US)

( * ) Notice: Subject to any disclaimer, the term of this patent is extended or adjusted under 35 U.S.C. 154(b) by 595 days.

(21) Appl. No.: 17/716,559

(22) Filed: Apr. 8, 2022

(65) Prior Publication Data
US 2022/0226523 A1 Jul. 21, 2022

Related U.S. Application Data

(63) Continuation-in-part of application No. 17/190,731, filed on Mar. 3, 2021, now Pat. No. 12,091,332,
(Continued)

(51) Int. Cl.
*A61L 2/18* (2006.01)
*B08B 3/02* (2006.01)

(52) U.S. Cl.
CPC ............. *A61L 2/183* (2013.01); *B08B 3/026* (2013.01); *A61L 2202/11* (2013.01); *A61L 2202/16* (2013.01)

(58) Field of Classification Search
CPC .. A61L 2/183; A61L 2202/11; A61L 2202/16; A61L 2/202; A61L 2202/02;
(Continued)

(56) References Cited

U.S. PATENT DOCUMENTS 9,079,227 B2 7/2015 Barnes
9,540,259 B2 1/2017 Lutz et al.
(Continued)

FOREIGN PATENT DOCUMENTS

CN 111214684 A 6/2020
CN 211865528 U 11/2020
(Continued)

OTHER PUBLICATIONS

"2020 new innovated Portable USB Electrolytic Ozone Generator active oxygen water", Alibaba.com, retrieved from: https://www.alibaba.com/product-detail/2020-new-innovated-Portable-USB-Electrolytic_1700000972371.html?spm=a2700.galleryofferlist.normal_offer.d_image.6e7e31fcPCwZUf, (Video Submission), retrieved on Dec. 21, 2020.
(Continued)

Primary Examiner — Xiuyu Tai
(74) Attorney, Agent, or Firm — Caesar Rivise, PC

(57) ABSTRACT

An apparatus that can be connected to a conventional sprayer bottle that permits the sprayer bottle to generate ozonated and ionized water to be used as a cleaning fluid. The apparatus includes an ozonator element submerged in the bottle water via a first electrical conductor and an ionizer lead submerged in the water via a second electrical conductor which is connected to an ionizer that is not submerged. Respective apertures are formed in the sidewall of the bottle, each having respective electrical connectors to permit the respective electrical connections to different power sources. The dip tube of the spray head is then passed through the top opening and into the water in the bottle and the spray head is secured onto the bottle. Electrical energy is provided through the respective conductors to ozonate and ionize the water in the bottle for use a cleaning agent. Humidifier or
(Continued)

Figure 1:
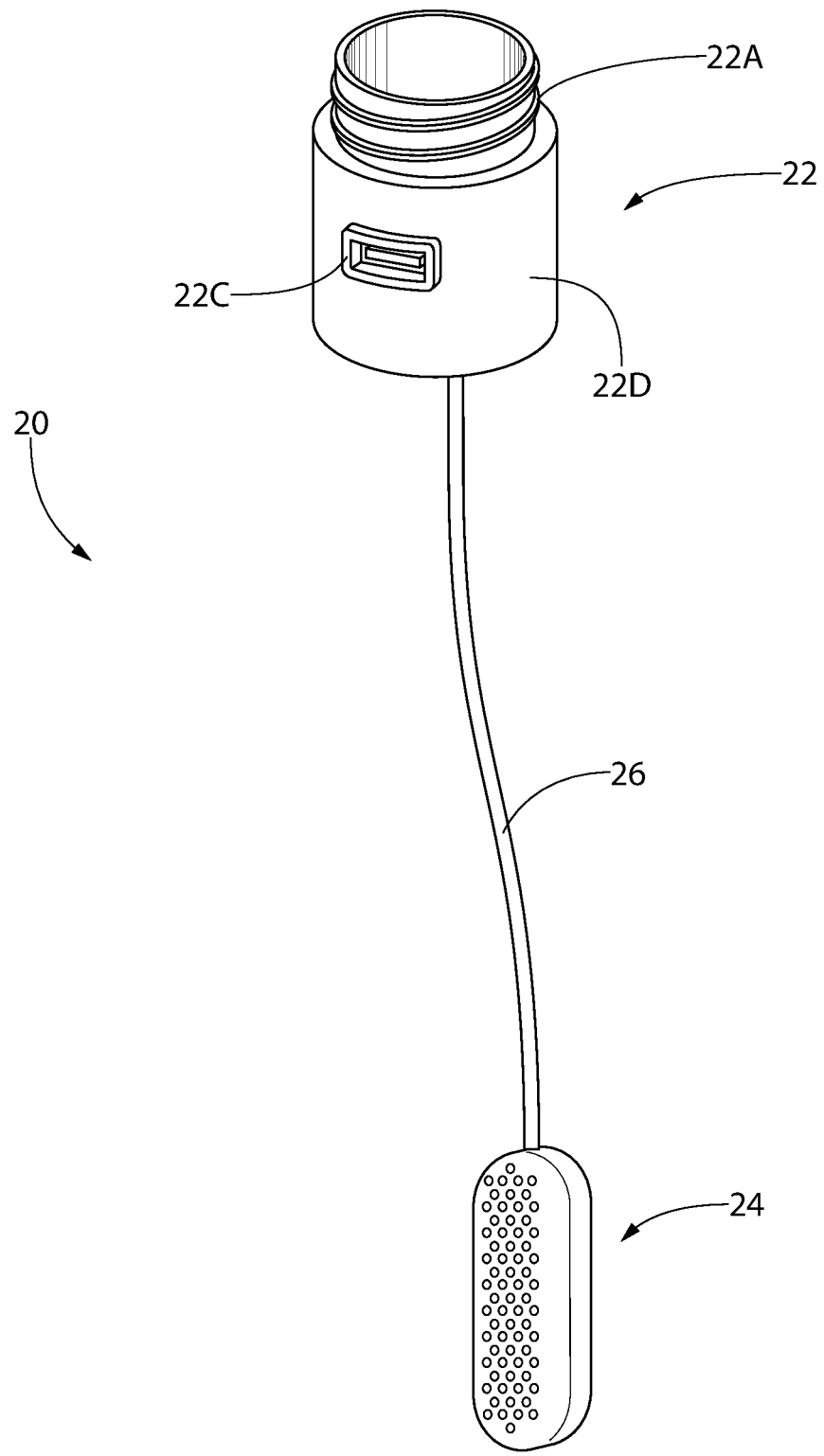

vaporizer versions of this invention provide an ozonated and ionized water mist or vapor.

23 Claims, 29 Drawing Sheets

Related U.S. Application Data which is a continuation-in-part of application No. 17/129,196, filed on Dec. 21, 2020, now Pat. No. 10,973,938.

(58) Field of Classification Search
CPC .......... B08B 3/026; C25B 1/13; C25B 15/00; C25B 9/30; C25B 11/02; C01B 13/10; C02F 1/78; C02F 1/281; C02F 2001/46133; C02F 9/00; C02F 2001/46123; C02F 1/283; C02F 1/06; C02F 2101/20; C02F 1/46104; C02F 2001/46166; C02F 2201/782; C02F 2201/46195; C02F 2001/427; C02F 2001/46142; C02F 2209/006; C02F 2201/784; C02F 2001/46185; C02F 2303/04; C02F 2201/78; C02F 1/46109; C02F 1/4672

See application file for complete search history.

(56) References Cited

U.S. PATENT DOCUMENTS

| | | | |
|---|---|---|---|
| 9,636,715 B1 | 5/2017 | Barnes | |
| 10,413,925 B2 | 9/2019 | Gonzalez et al. | |
| 10,610,902 B1 | 4/2020 | Brook et al. | |
| 10,973,938 B1 | 4/2021 | Graham | |
| 2002/0185423 A1* | 12/2002 | Boyd | C25B 15/00 210/167.3 |
| 2007/0023273 A1 | 2/2007 | Kitaori et al. | |
| 2009/0039033 A1 | 2/2009 | Kee et al. | |
| 2013/0277211 A1 | 10/2013 | Joshi et al. | |
| 2016/0097132 A1 | 4/2016 | Joshi et al. | |
| 2017/0137953 A1 | 5/2017 | Jonte et al. | |

FOREIGN PATENT DOCUMENTS

| | | |
|---|---|---|
| CN | 211914361 U | 11/2020 |
| KR | 20170011173 A | 2/2017 |
| KR | 20170063361 A | 6/2017 |
| KR | 20190003057 A | 1/2019 |
| WO | WO 2013/154914 | 10/2013 |

OTHER PUBLICATIONS

"Timer Relay, DROK Time Delay Relay DC 5V 12V 24V Delay Controller Board Delay-off Cycle Timer 0.01s-9999mins Trigger Delay Switching Relay Module with LCD Display Support Micro USB 5V Power Supply", Amazon.com, retrieved from: https://www.amazon.com/gp/product/B07DFT2WDS/ref=ox_sc_act_title_1?smid=AFHAE9RJVUMB&psc=1, retrieved on Dec. 21, 2020.
"Electrolytic Ozone Generator", Alibaba.com, retrieved from: https://mac-verin.en.alibaba.com/, retrieved on Dec. 21, 2020.
English abstract of KR20190003057A.
International Search Report for related PCT Application No. PCT/US2021/062789 dated Apr. 20, 2022.

\* cited by examiner

APPARATUS AND METHOD FOR MODIFYING A SPRAYER BOTTLE INTO AN OZONATING AND IONIZING WATER SPRAYER BOTTLE AND FOR PROVIDING HUMIDIFICATION WITH OZONATED AND IONIZED WATER

CROSS-REFERENCE TO RELATED APPLICATIONS

This Continuation-in-Part application claims the benefit under 35 U.S.C. § 120 of application Ser. No. 17/190,731 filed on Mar. 3, 2021 entitled APPARATUS AND METHOD FOR MODIFYING A SPRAYER BOTTLE INTO AN OZONATING SPRAYER BOTTLE AND FOR MAKING A WATER RESERVOIR INTO AN OZONATED WATER RESERVOIR which in turn is a Continuation-in-Part application, and claims the benefit under 35 U.S.C. § 120, of application Ser. No. 17/129,196 (now U.S. Pat. No. 10,973,938) filed on Dec. 21, 2020 entitled INSERT FOR SPRAYER BOTTLE FOR OZONATING WATER and all of whose entire disclosures are incorporated by reference herein.

BACKGROUND OF THE INVENTION

The present invention relates to relates generally to cleaning products that generate ozonated water and, more particularly, to an assembly that can be inserted into conventional spraying bottles for producing ozonated water.

The use of ozone ($O_3$) in different forms for sanitization is well-known. As a gas, ozone can be used for destroying mold or allergens but must be carefully administered because those levels of gaseous ozone can also be toxic to small children, pets and plants. However, when used in water, such ozonated water can be used to safely disinfect items or surfaces; in fact, ozonated water can even be ingested safely; for example, ozonated water is used by campers to clean water by destroying bacteria and other undesired content therein.

Devices that generate ozone are known as "ozonizers". Conventional ozonizers typically utilize electricity, or exposure to ultraviolet radiation, to convert oxygen ($O_2$) to ozone ($O_3$). The following U.S. patent references show examples of devices utilizing ozonated water. U.S. Pat. No. 9,079,227 (Barnes); U.S. Pat. No. 9,636,715 (Barnes); U.S. Pat. No. 9,540,259 (Lutz, et al.); U.S. Pat. No. 10,610,902 (Brook, et al.); U.S. Patent Publication Nos. 2013/0277211 (Joshi, et al.), now abandoned; and 2016/0097132 (Joshi, et al.), now abandoned.

While the devices disclosed in the aforementioned publications may be generally suitable for their intended purposes, these devices do not provide for convenient method of converting a conventional spray bottle into spray bottle of ozonated water. Thus, there remains a need for an insert that can be easily connected to a conventional spray bottle for generating ozonated water to act as a cleaning fluid, or for use as potable water. Moreover, there remains a need for easily making a water reservoir (e.g., a water tank) an ozonating source of water, for example, a potable water source. Furthermore, there also remains a need for ionizing the water also so that the output of the sprayer bottle comprises a combination of an ozonated and ionized water mist. There also remains a need for making the ozonated source of water also an ionized source of water. Finally, there remains a need for providing humidification that comprises an ozonated and ionized water mist or vapor output.

All references cited herein are incorporated herein by reference in their entireties.

BRIEF SUMMARY OF THE INVENTION

An apparatus for permitting a conventional spray bottle to generate ozonated and ionized water, wherein the conventional spray bottle has a spray head and bottle portion, is disclosed. The apparatus comprises: first and second electrical connectors associated with the bottle portion; an ozonator element that is coupled to the first electrical connector via an electrical cable and wherein the ozonator element is configured to be submerged within the water contained within the bottle portion; an ionizer lead that is coupled to the second electrical connector and wherein the ionizer lead is configured to be submerged within the water contained in the bottle portion; wherein the first electrical connector conveys electrical power to the ozonator element to activate the ozonator element to ozonate the water contained in the bottle portion and wherein an ionizer is also coupled to the second electrical connector for energizing the ionizer lead to ionize the water contained in the bottle portion.

An apparatus for generating an ozonated and ionized water mist or vapor is disclosed. The apparatus comprises: a housing configured to contain water; an ozonator element that is configured to be submerged within the water and which is coupled to electrical power via a first conductor to ozonate the water in the housing; an ionizer having an ionizer lead, wherein the ionizer lead is configured to be submerged within the water, and wherein the ionizer is coupled to electrical power via a second conductor to ionize the water in the housing; and an energizing element that is configured to be submerged within the water and which is coupled to electrical power via a third conductor for converting the ozonated and ionized water into an ozonated and ionized mist or vapor.

A method of ozonating and ionizing water in a conventional spray bottle having a spray head with a dip tube and a bottle portion is disclosed. The method comprises: providing an insert member having an internal passageway and wherein the insert member can be releasably inserted between the spray head and the bottle portion, wherein the insert member further comprises an ozonator element that is coupled to the insert member via an electrical cable and an ionizer lead that is electrically coupled to the insert member; submerging the ozonator element and the ionizer lead within the water contained within the bottle portion; inserting the dip tube through the insert member and into the bottle portion; releasably securing a first end of the insert member to an opening in the bottle portion and a second end, opposite the first end, of the insert member to the spray head; applying electrical power to the insert member to activate the ozonator element to ozonate the water in the bottle portion and to an ionizer that is electrically coupled to the insert and to the ionizer lead to also ionize the water in the bottle portion.

Figure 2:
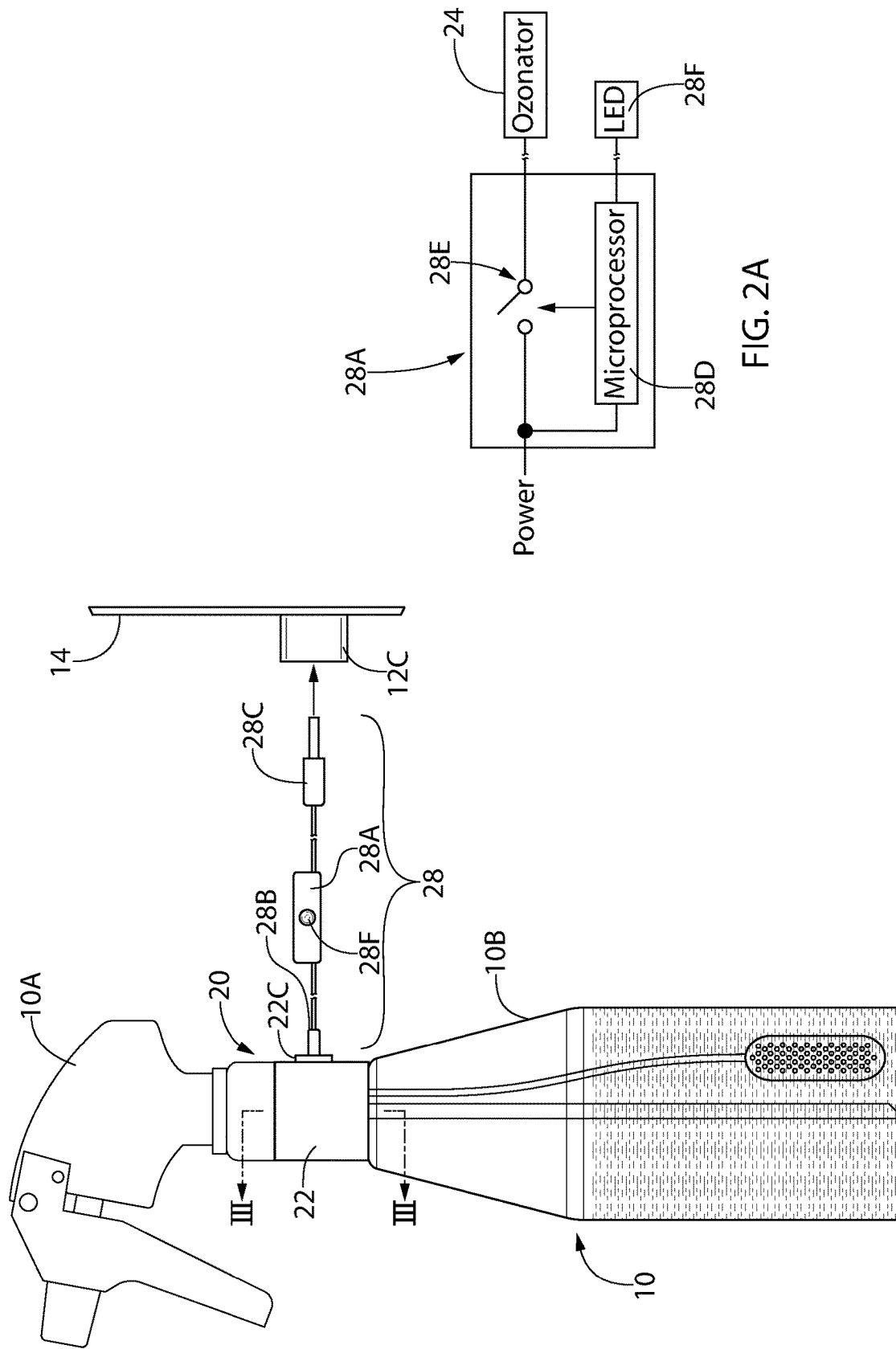
Figure 3:
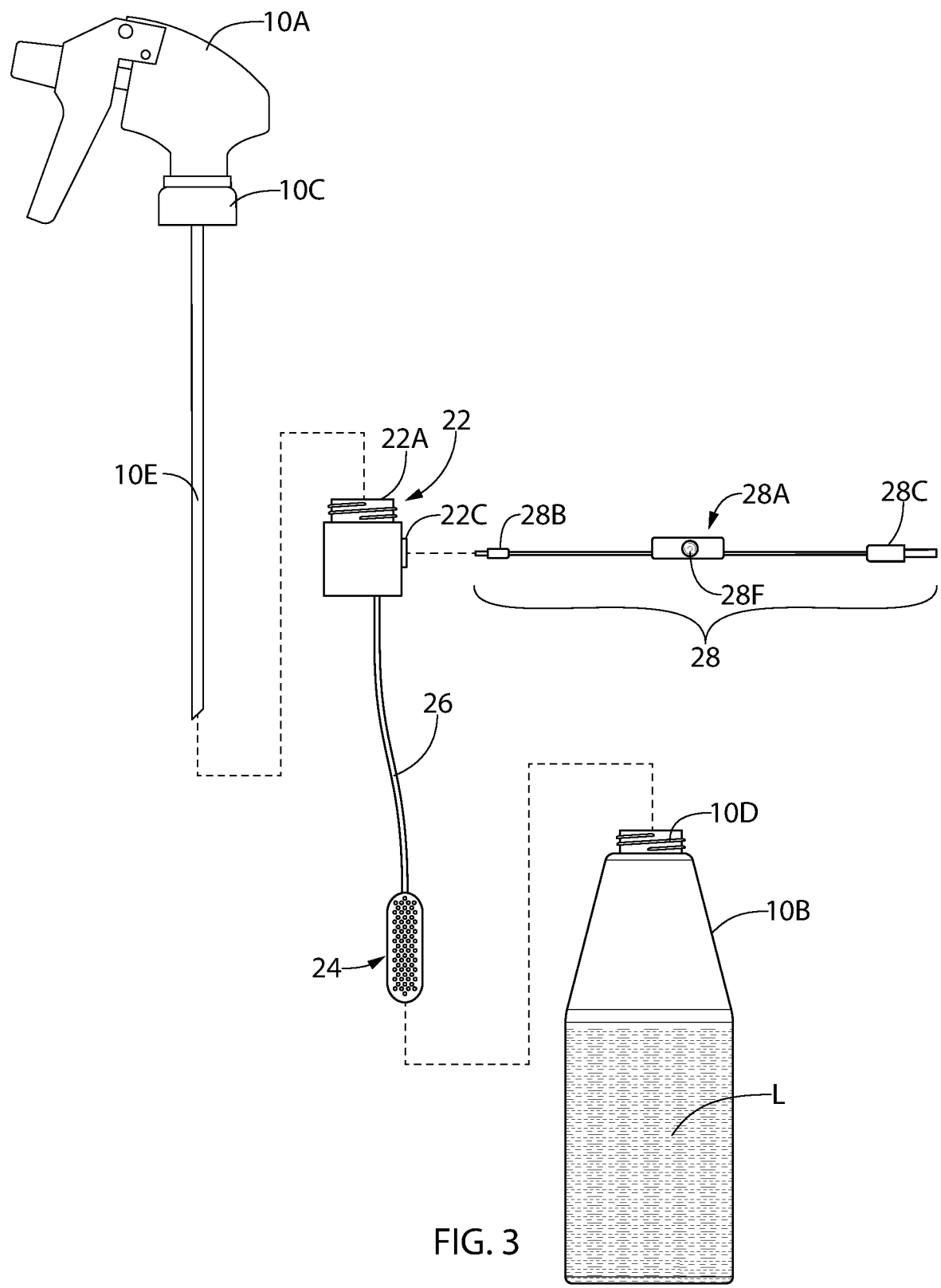

A method of ozonating and ionizing water in a conventional spray bottle having a spray head with a dip tube and a bottle portion having a top opening is disclosed. The method comprises: forming two apertures in a sidewall of the bottle portion; securing a first electrical connector in one of the apertures and to which an ozonator element is electrically connected via a first electrical cable and securing a second electrical connector in the other one of the apertures and to which an ionizer lead is electrically connected; passing the ozonator element and the ionizer lead through the top opening and into the interior of the bottle portion; disposing water into the bottle portion through the top opening; inserting the dip tube through the top opening and into the bottle portion and releasably securing the spray head to the bottle portion; and coupling a first power cord to the first electrical connector to provide electrical power to activate the ozonator element to ozonate the water in the bottle portion and coupling a second power cord, having an ionizer, to the second electrical connector to provide electrical power to activate the ionizer lead to ionize the water in the bottle portion.

A method of generating an ozonated and ionized water mist or vapor is disclosed. The method comprises: disposing water in a container; submerging an ozonator element within the water and which is coupled to electrical power via a first conductor to ozonate the water in the container; submerging an ionizer lead within the water and wherein the ionizer lead is electrically coupled to an ionizer which is coupled to electrical power via a second conductor to ionize the water in the container; and submerging an energizing element within the water and which is coupled to electrical power via a third conductor for converting the ozonated and ionized water into an ozonated and ionized mist or vapor.

BRIEF DESCRIPTION OF SEVERAL VIEWS OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 depicts the insert assembly of the present invention;

FIG. 2 depicts the insert assembly of the present invention installed in a conventional spray bottle with a power cord coupled to the insert for energizing the ozonator element;

FIG. 2A is a schematic of the electronics of the present invention;

FIG. 3 is an exploded view of the present invention installed in a conventional spray bottle along with the power cord;

FIG. 4 is a cross-sectional view of the insert member taken along line of FIG. 2;

FIG. 5 is a flow diagram of the microprocessor operation in the electronics;

FIG. 5A is a flow diagram of the process of using the present invention in a conventional spray bottle;

FIG. 6 is a partial view of an alternative insert member of the present invention which includes a spout and corresponding closure shown in an exploded condition;

FIG. 7 is a partial back view of the alternative insert member of FIG. 6;

FIG. 8 shows an alternative apparatus for modifying a sprayer bottle into an ozonating sprayer bottle;

FIG. 9 depicts the alternative apparatus of FIG. 8 installed in a conventional spray bottle with a power cord coupled to the alternative apparatus for energizing the ozonator element;

FIG. 9A is a schematic of the electronics of the alternative apparatus;

FIG. 10 is an exploded view of the alternative apparatus installed in a conventional spray bottle along with the power cord;

FIG. 11 is a flow diagram of the process of using the alternative in a conventional spray bottle;

FIG. 12 is a functional diagram of an inventive coupler for modifying a water reservoir into an ozonating water reservoir;

FIG. 13 depicts a second embodiment of the insert assembly of the present invention which uses both an ozonator element and an ionizer/ionizer lead;

FIG. 14 depicts the second embodiment of the insert assembly of the present invention installed in a conventional spray bottle with respective power cords coupled to the insert for energizing the ozonator element and the ionizer lead;

FIG. 15 is an exploded view of the second embodiment of the insert assembly installed in a conventional spray bottle along with the respective power cords;

FIG. 16 is a cross-sectional view of the second embodiment of the insert member taken along line XVI-XVI of FIG. 14;

FIG. 17 shows a second embodiment to the alternative apparatus for modifying a sprayer bottle into an ozonating and ionizing sprayer bottle;

FIG. 18 depicts the second embodiment of the alternative apparatus of FIG. 17 installed in a conventional spray bottle with respective power cords coupled to the ozonator element and to the ionizer lead;

FIG. 19 is an exploded view of the second embodiment of the alternative apparatus installed in a conventional spray bottle along with respective power cords coupled to the ozonator element and to the ionizer lead;

FIG. 20 is an isometric view of a humidifier or vaporizer of the present invention that generates an ozonated and ionized water vapor;

FIG. 21 is a block diagram of the electronics of the humidifier or vaporizer of FIG. 20;

FIG. 22 is flow diagram the process of using the humidifier or vaporizer of the present invention;

FIG. 23 depicts an alternative portable ozonated/ionized water misting/cleaning tool;

FIG. 24 is isometric view of the tool of FIG. 23 with the carrier lid opened;

FIG. 24A is side view of the carrier portion of the tool;

FIG. 25 is a partial top view of the interior of the carrier portion with carrier lid opened;

FIG. 26 is a partial view of the container insider the carrier portion with the container lid opened; and FIG. 27 depicts some exemplary cleaning accessories, shown partially, that can be coupled to the container.

DETAILED DESCRIPTION OF THE PREFERRED EMBODIMENTS

Referring now to the figures, wherein like reference numerals represent like parts throughout the several views, exemplary embodiments of the present disclosure will be described in detail. Throughout this description, various components may be identified having specific values, these values are provided as exemplary embodiments and should not be limiting of various concepts of the present invention as many comparable sizes and/or values may be implemented.

FIG. 1 depicts the insert assembly 20 of the present invention which comprises an insert member 22 and an ozonator element 24 (e.g., a portable electrolytic ozone generator such as the Moreclean Electrolyzed Ozone Generator sold by Alibaba.com) that is coupled to the insert member 22 via an electrical cable 26. The insert member 22 comprises an upper thread 22A (e.g., a threaded male connector) for engaging a corresponding threaded collar 10C in a spray head 10A of a conventional spray bottle 10 (FIGS. 2-3). The insert member 22 also comprises a lower thread 22B (e.g., a threaded female connector, see FIG. 3) for engaging a corresponding thread 10D on the top of a bottle portion 10B of the conventional spray bottle 10. The insert member 22 further comprises an electrical connector 22C (e.g., a USB receptacle) in a sidewall 22D of the insert member 22. To the internal side 22E of the electrical connector 22C is fixedly secured a first end of the electrical cable 26 for powering the ozonator element 24 coupled at the other end of electrical cable 26.

Figure 4:
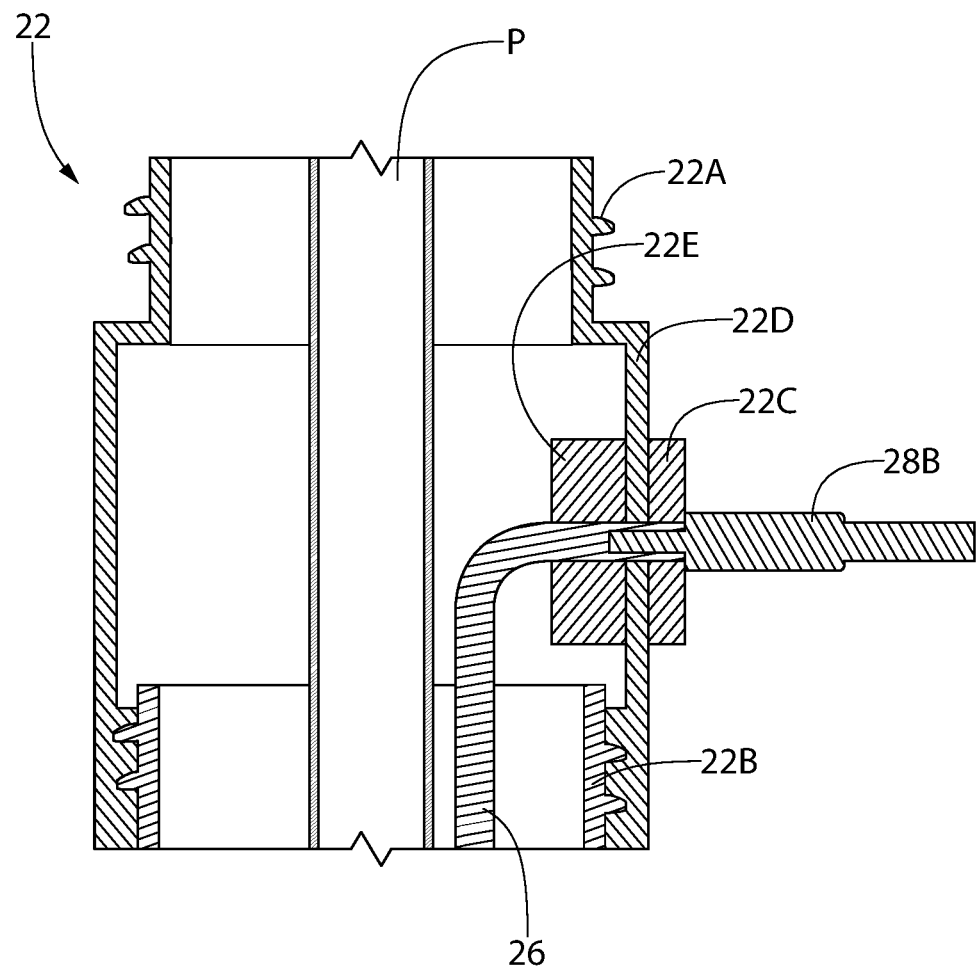

As can be seen from FIG. 4, the insert member 22 basically forms a passageway P to allow the spray head dip tube 10E (FIG. 3) to easily pass therethrough and into the water L in the bottle portion 10B, as well as allowing the ozonator element 24 to be suspended inside the water L in the bottle portion 10B. (See FIG. 2). As such, the internal volume of the insert member 22 provides sufficient space or passageway for the dip tube 10E and the electrical cable 26 to pass easily into the opening to the bottle portion 10B. The insert member 22A may comprise a durable plastic material, e.g., PVC or ABS.

As mentioned previously, the ozonator element 24 may comprise a commercially-available portable electrolytic ozone generator. This ozonator element 24 draws very little electrical current and, as such, it is safe to use while it is submerged in the water L (e.g., tap water). To ozonate the water in the bottle portion 10B, the ozonator element 24 need only be activated for a relatively short period of time, e.g., two minutes. This activation period (AP) may vary depending on the purity of the water. Once the ozonator element 24 is activated for the predetermined AP, the water L in the bottle portion 10B is "ozonated" and is ready for use as a cleaning or sanitizing agent (or potable water). Once "ozonated", the water L in the bottle portion 10B will remain "ozonated" for approximately two hours. After that time, the ozonated state of the water L will return to its pre-ozonated state and will need to be "re-ozonated" to form a cleaning agent (or potable water) again. Although this "effective use period" (EUP) may vary, two hours is a reliable time for using the ozonated water as a cleaning agent before the water L requires re-ozonation.

One of the key aspects of the present invention 20 is to provide a "ready-to-use" ozonated cleaning product in a conventional spray bottle 10. This is accomplished by electronics associated with the insert assembly 20. In one embodiment, a power cord 28 is also provided that includes a controller 28A, a first USB connector 28B and a second USB connector 28C. The first USB connector 28B connects to the electrical connector 22C in the insert member 22 while the second USB connector 28C connects to a conventional USB wall plug converter 12 which is inserted into a conventional wall power outlet 14. As shown most clearly in FIG. 2A, the controller 28A comprises a microprocessor 28D (e.g., microcontroller such as Microchip ATTINY 4-MAHR etc.), a switch 28E (e.g., a solid-state switch, e.g., NPN, transistor, etc.) and an indicator 28F (e.g., a light-emitting diode (LED), e.g., a Cree Inc. C512A-WNN-CZ0B0151 LED).

Figure 5:
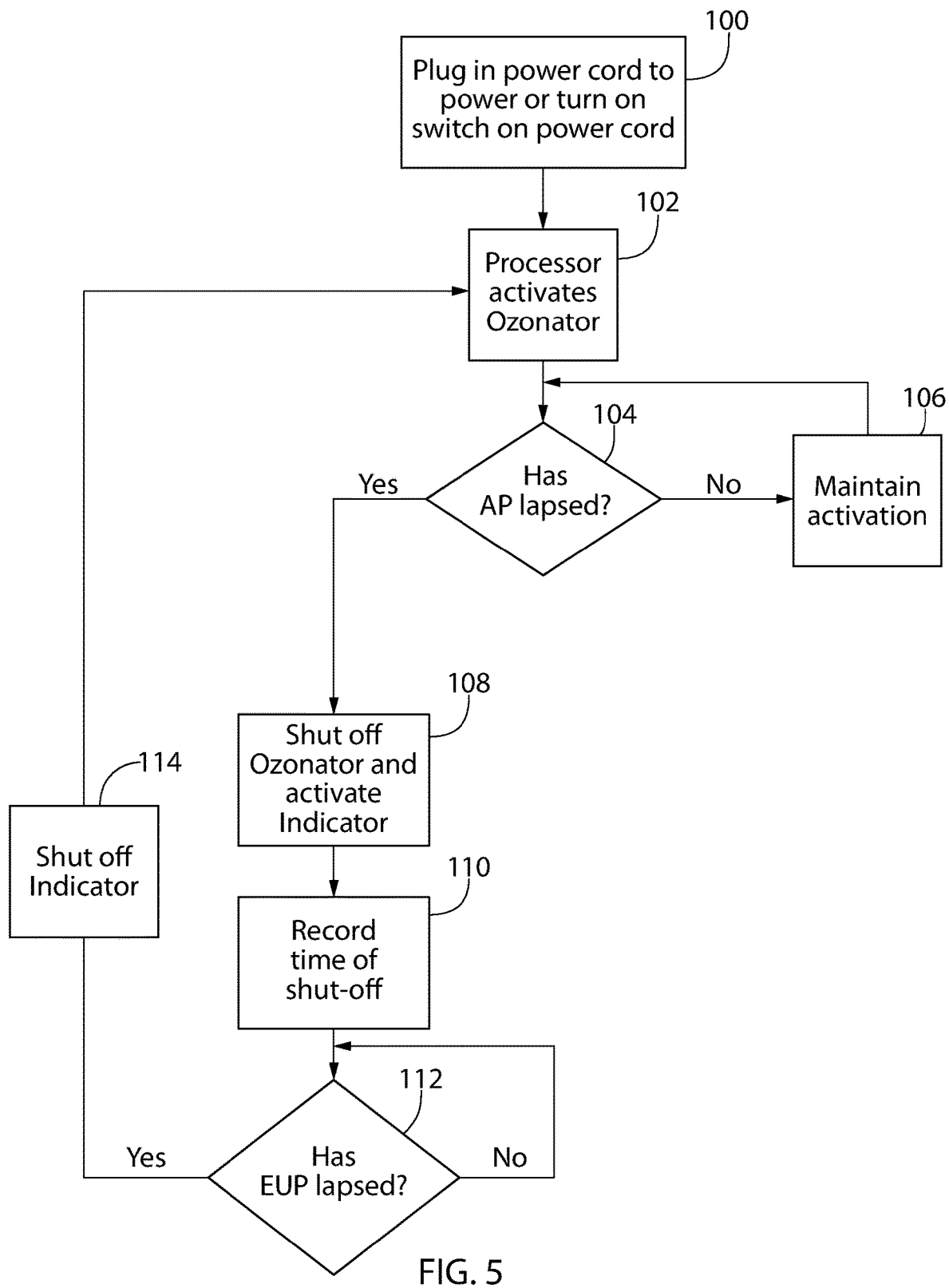

FIG. 5 depicts the microprocessor 28D operation with the bottle portion 10B filled and the insert assembly 20 installed and the spray head 10A installed. Once the power cord 28 is plugged into the connector 22C (step 100), the microprocessor 28D turns on the ozonator element 24 (step 102) and monitors the AP to determine if the AP has elapsed (step 104) or not (step 106). If the AP has elapsed, the microprocessor 28D shuts off the ozonator element 24 by opening the switch 28E and turns on the indicator 28F (step 108). The lighted indicator 28F lets the user know that he/she has a fully ozonated cleaning product ready for use. The microprocessor 28D notes the timestamp of the shut-off of the ozonator element 24 (step 110). The microprocessor 28D then monitors how much time has elapsed since the shut-off timestamp (step 112) to determine if the predetermined EUP has lapsed. If it has, the microprocessor 28D shuts of the indicator 28F (step 114) and immediately activates the ozonator element 24 (step 102) to re-ozonate the water L. As a result, this process guarantees that if a spray bottle 10 with the insert assembly 20 installed therein is plugged into wall power and no one has used the spray bottle, the water L is automatically re-ozonated after every EUP has lapsed.

Figure 5A:
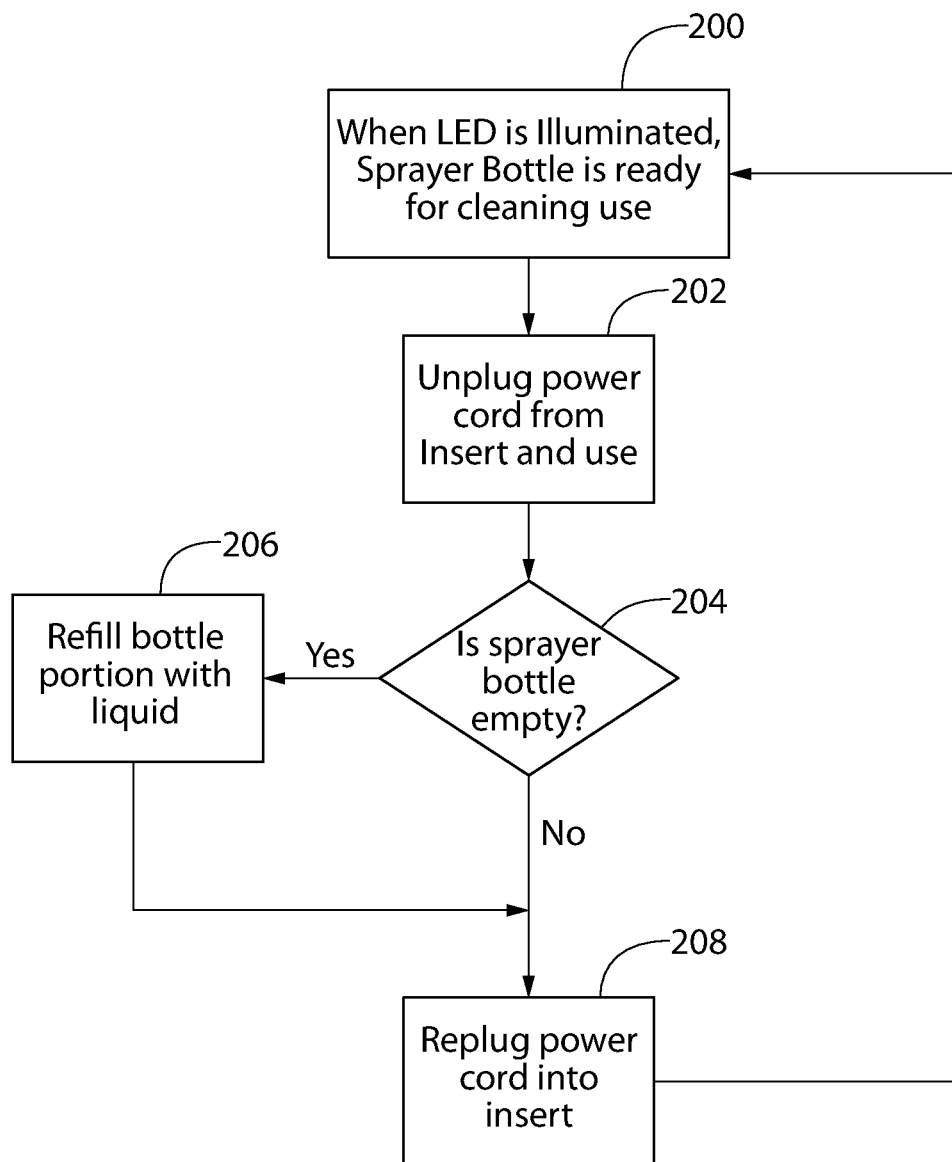

FIG. 5A provides a flow diagram of the use of the spray bottle 10 with the insert assembly 20 installed therein and powered as describe above. With the indicator 28F illuminated (step 200), the user unplugs the power cord (step 202) by disengaging the USB connector 28B from the insert connector 22C. The user can now use the spray bottle 10 to clean. If the user empties the bottle portion 10B (step 204), the user will refill the bottle portion 10B (step 206) and then reconnect the power cord to the insert member 22 (step 208). Should the user not empty the bottle 10 and reconnects the power cord to the insert member 22, the microprocessor 28D will re-ozonate the remaining water L in the bottle portion 10B, even if the EUP has not lapsed; there is no concern in "re-ozonating" water L that is still within the EUP.

Figure 6:
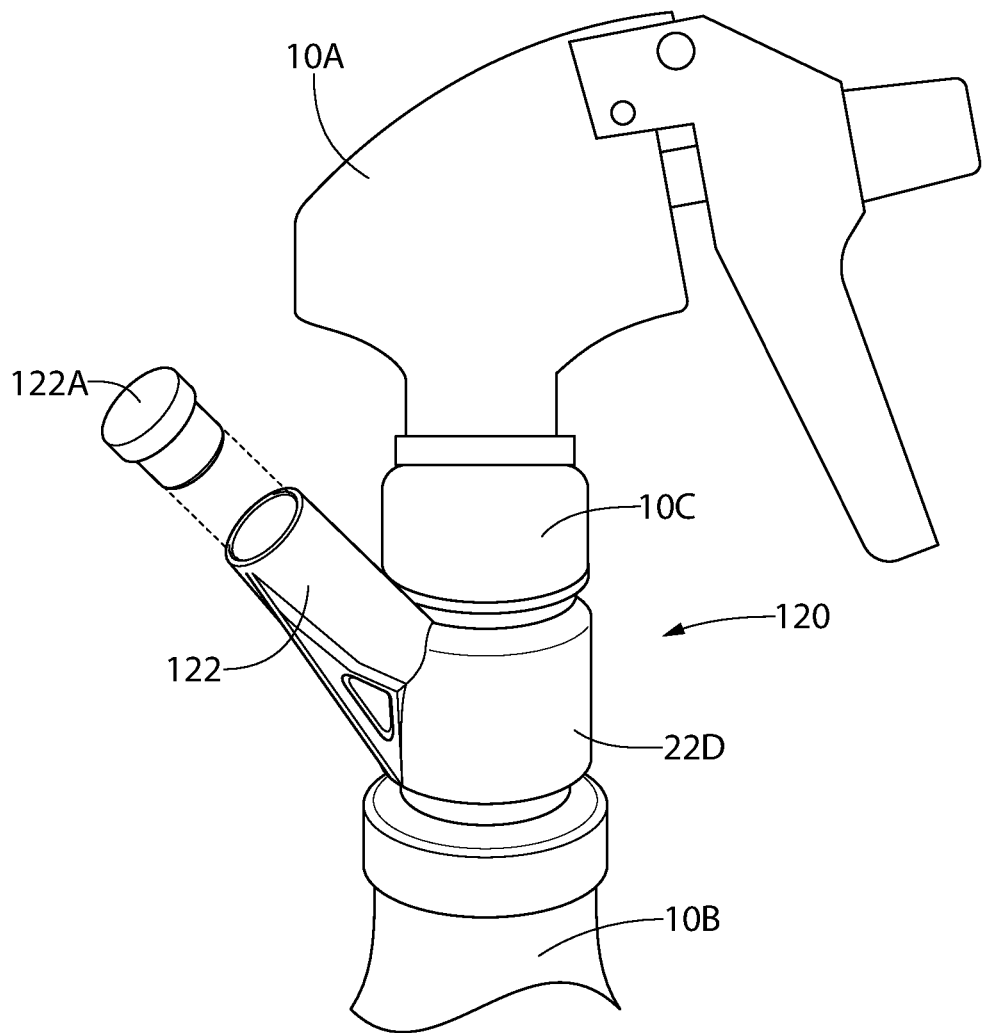
Figure 7:
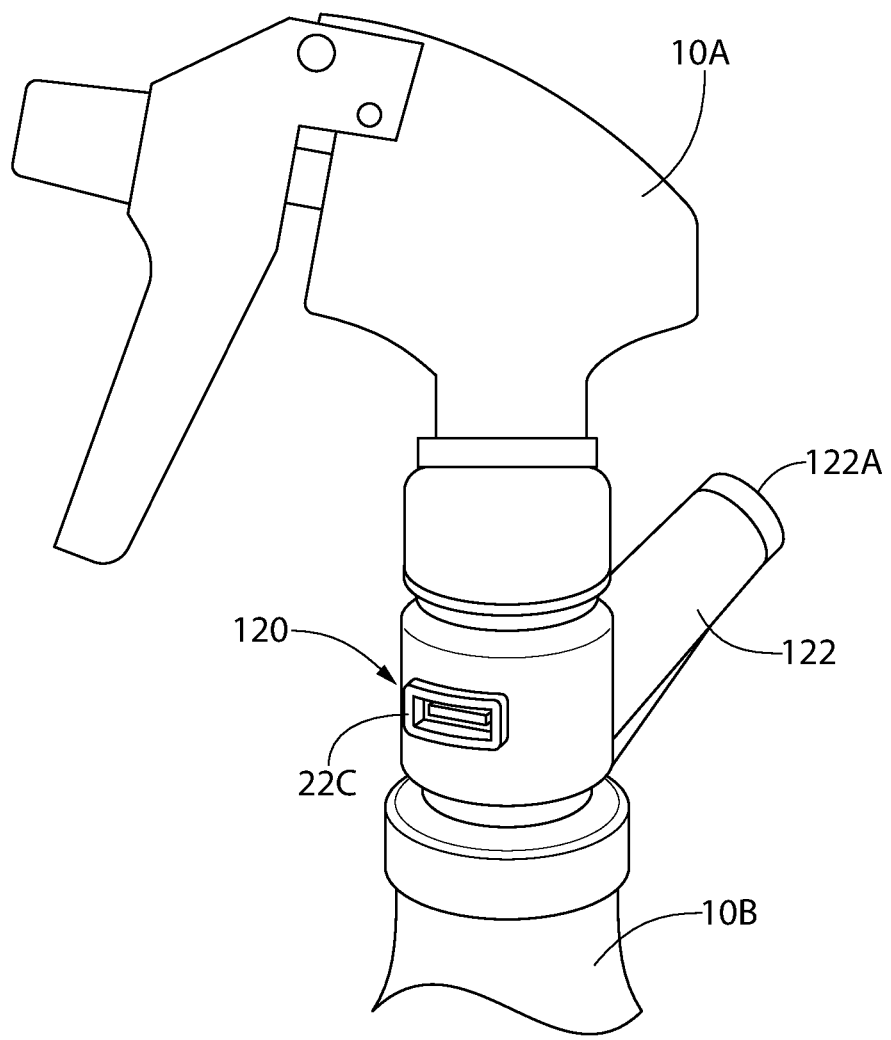

To make the use of the insert assembly even more convenient, an alternative insert assembly 120 is shown in FIGS. 6-7. The alternative insert assembly 120 is identical to the insert assembly 20 but includes a refill spout 122 with an associated removable closure 122A. As discussed above, when the ozonated water L is emptied from the bottle 10B in step 206, the user needs to refill the bottle portion 10B. Instead of having to disengage the spray head 10A or the insert assembly 22 from the bottle portion 10B, the user can simply remove the closure 122A (e.g., a cap), pour in more water L and then reinstall the closure 122A. The user then inserts the power cord 28 to the connector 22C in the insert member 120 and the process of FIG. 5 is carried out.

It should be noted that the use of USB connectors is simply by way of example and that it is within the broadest scope of the invention 20/120 to include all types of electrical connectors for powering the ozonator element 24 and controlling its energization. Furthermore, it is within the broadest scope of the invention to include the controller 28A on the insert member 22 itself, rather than in the power cord 28. Moreover, it is also within the broadest scope of the invention 20/120 to utilize a replaceable battery or a rechargeable battery on or within the insert assembly 20/120.

A key aspect to this invention 20/120 is that power to the ozonator element 24 is being provided from the insert member 22 either from an external power source (e.g., a wall outlet, etc.) or from an on-board power source (e.g., a replaceable battery or a rechargeable battery, etc.) associated with the insert member 20/120. Furthermore, where the controller 28A itself is located within or on the insert member 22, an exemplary module such the DROK Time Delay Relay DC 5V-12V-24V Delay Controller Board Delay-Off Cycle Timer board may be used.

It is also within the broadest scope of the present invention to include a user interface with the controller 28A that would permit the user to adjust the AP based on the purity of the water being used in the sprayer bottle 10, as well as being able to adjust the EUP to ensure that ozonated water is always present in the sprayer bottle 10.

It is also within the broadest scope of the present invention 20 to provide an alternative use of the ozonated water within the sprayer bottle: a potable water source, especially in emergencies. The ozonated water in the sprayer bottle 10 can also act as potable water, in addition to the primary use of the ozonated water as cleaning agent.

Figure 8:
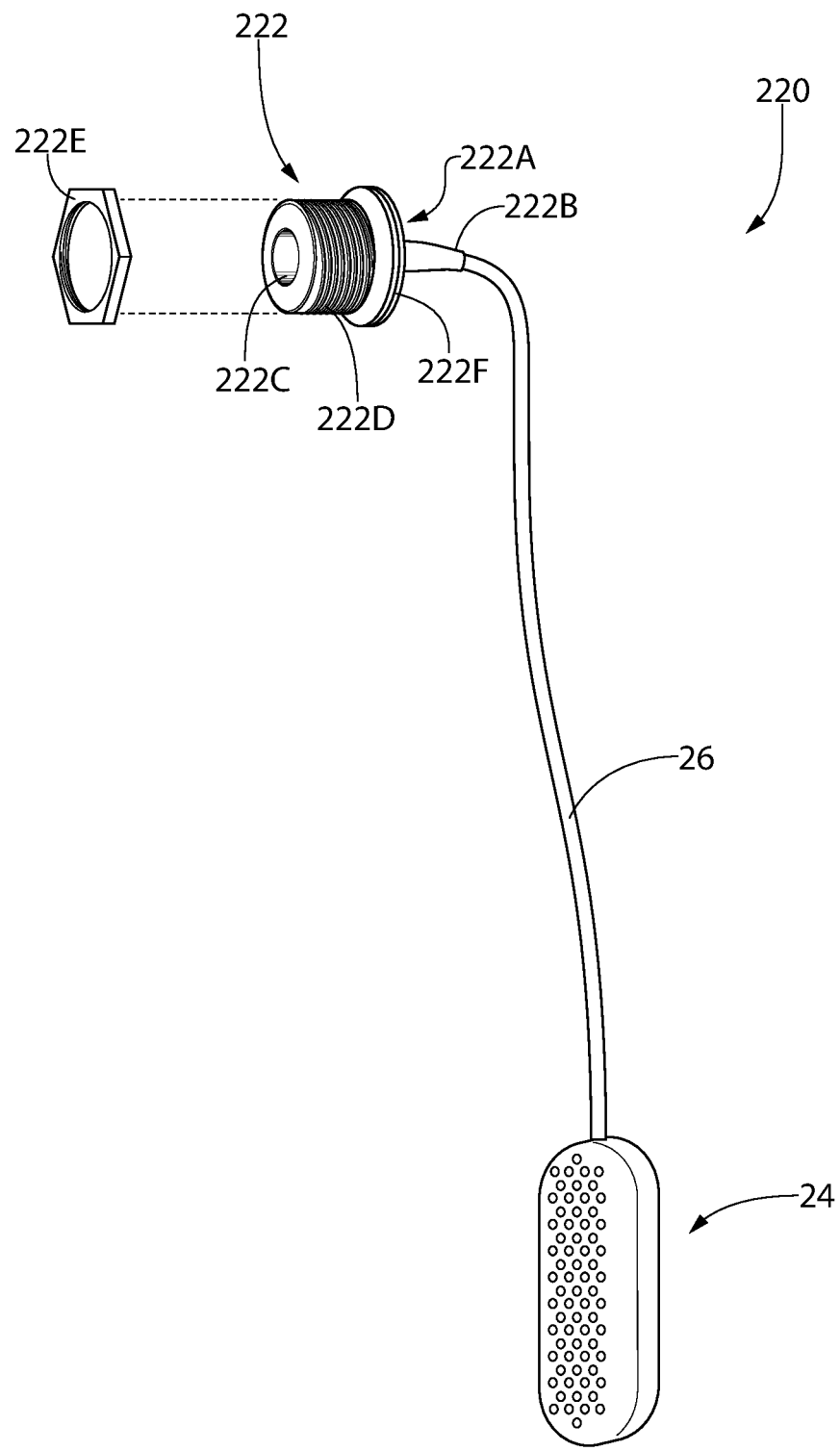

FIGS. 8-11 depict an alternative apparatus 220 for converting a conventional sprayer bottle 10 into an ozonating sprayer bottle. In general, rather than installing the insert 22 between the sprayer head 10A and the bottle portion 10B as described above, in the alternative apparatus 220, the ozonator element 24/electrical cable 26 have an electrical connector 222 coupled to the other end of the cable 26 which is installed into the wall itself of the bottle portion 10B. As shown in FIG. 8, the alternative apparatus 220 comprises the ozonator element 24 coupled to one end of the electrical cable 26. The other end of the electrical cable 26 is coupled (e.g., soldered) to one side 222A of the electrical connector 222 which is then covered with a shrink wrap 222B. The opposite side of the connector 222 comprises an electrical receptacle 222C surrounded by a screw thread 222D having a corresponding nut 222E. A shoulder 222F provides a flange against which the connector 222 is able to seat against the internal wall of the bottle portion 10B, as described next.

Figure 9:
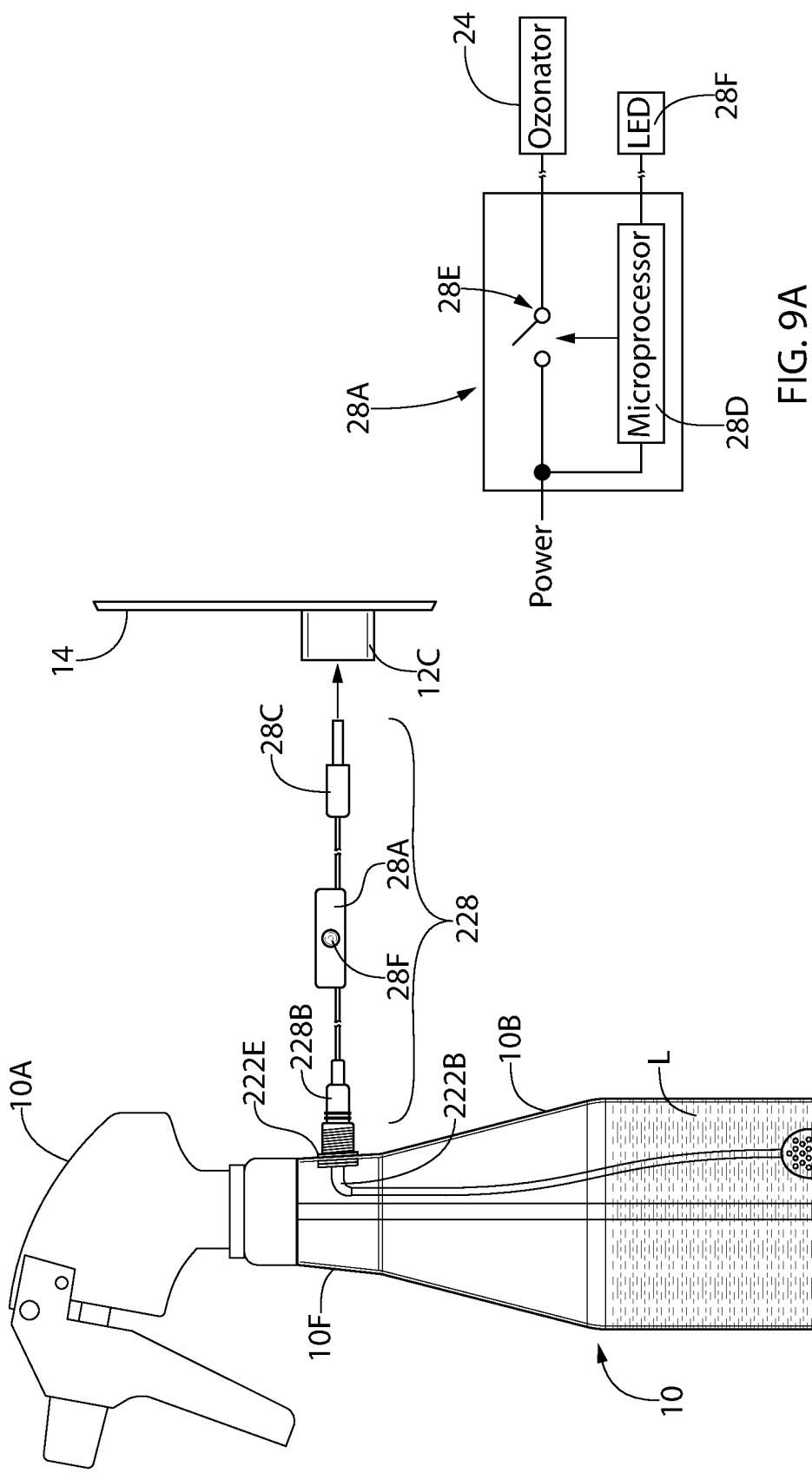
Figure 10:
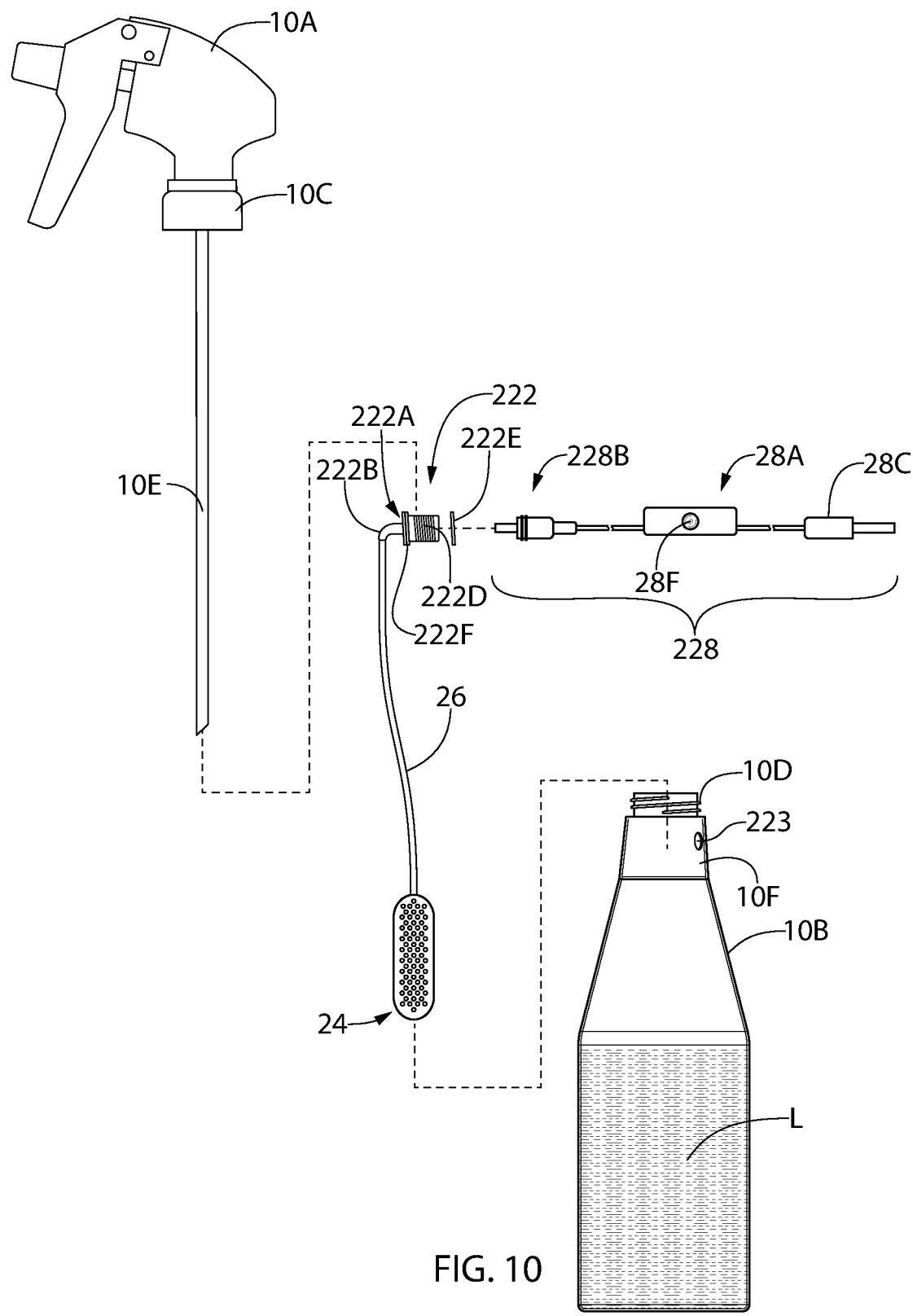

In particular, a hole 223 (FIG. 10) is drilled through a sidewall 10F of the sprayer bottle 10; it is preferable to have a vertical sidewall in the bottle as shown in FIGS. 9-10, although the hole 223 could just as easily have be formed in the tapered portion 10B. By way of example only, the hole 223 may be a ¼ inch hole. Next, the ozonator element 24 and electrical cable 26 are placed down through the open end of the bottle portion 10B, along with the connector 222. The electrical receptacle 222C and the screw thread 222D are then pushed through the hole 223 until the shoulder 222F is positioned against the inner side of the sidewall 10F and the nut 222E is threaded on the screw thread 222D and then tightened against the sidewall 10F, thereby releasably securing the connector 222 to the sidewall 10F. The stainless steel composition of the connector 222 prevents the connector 222 from rusting due to exposure to the water L and the shrink wrap 222B provides protection against rust as well against exposure of the soldered electrical connection to the water L also.

With the electrical connector 222 installed within the bottle sidewall 10F, the ozonator element 24 is ready for energization in the same manner as described for the insert 22. As described previously with regard to the insert 22, one of the key aspects of the alternative apparatus 220 is to provide a "ready-to-use" ozonated cleaning product in a conventional spray bottle 10. This is accomplished by electronics associated with the alternative apparatus 220. As shown most clearly in FIG. 10, a power cord 228 is also provided that includes the controller 28A, the USB connector 28C and a round DC power plug 228B that is received in the electrical receptacle 222C of the connector 222. As shown most clearly in FIG. 9A, the controller 28A comprises the microprocessor 28D (e.g., microcontroller such as Microchip ATTINY 4-MAHR etc.), the switch 28E (e.g., a solid-state switch, e.g., NPN, transistor, etc.) and the indicator 28F (e.g., a light-emitting diode (LED), e.g., a Cree Inc. C512A-WNN-CZ0B0151 LED). Operation of the microprocessor 28D is similar to the description above in accordance with FIG. 5.

Figure 11:
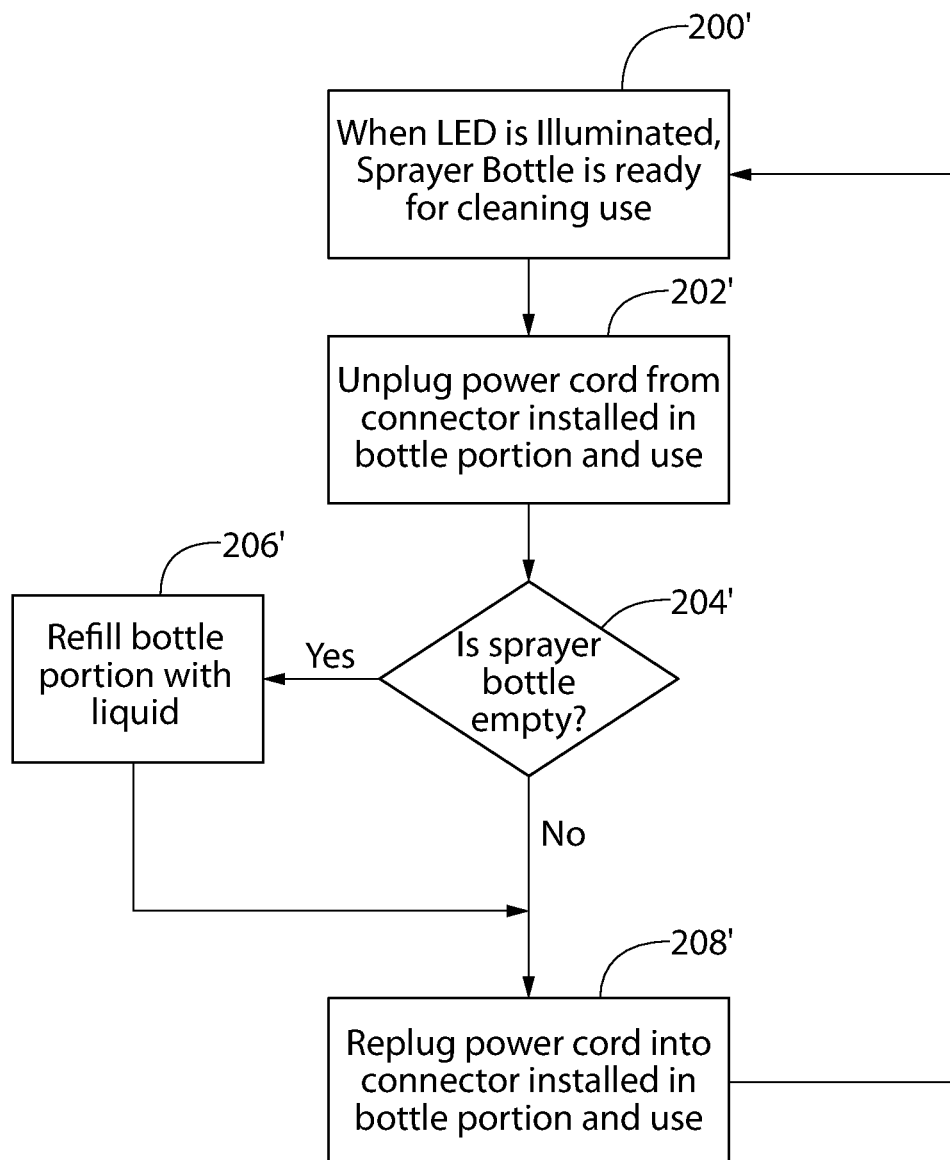

FIG. 11 provides a flow diagram of the use of the spray bottle 10 using the alternative apparatus 220 and powered as describe above. With the indicator 28F illuminated (step 200'), the user unplugs the power cord (step 202') by disengaging the DC power plug 228B from the connector 222. The user can now use the spray bottle 10 to clean. If the user empties the bottle portion 10B (step 204'), the user will refill the bottle portion 10B (step 206') and then reconnect the power cord to the connector 222 (step 208'). Should the user not empty the bottle 10 and reconnects the power cord to the connector 222, the microprocessor 28D will re-ozonate the remaining water L in the bottle portion 10B, even if the EUP has not lapsed; there is no concern in "re-ozonating" water L that is still within the EUP.

As can be appreciated, the alternative apparatus 220 provides another alternative to using the insert 22. The alternative apparatus 220 can be easily installed by a user by simply drilling the hole 223 in the sidewall 10F of the bottle portion 10B of the sprayer bottle 10B, positioning the ozonator element 24/electrical cable 26 down into the bottle portion 10B, inserting the screw threads 222D through the hole 223 and then using the screw threads 222D/nut 222E to lock the connector 222 into the sidewall 10F of the bottle portion 10B. Once installed, the alternative apparatus 220 operates identically as the insert 20. Another advantage of the alternative apparatus 220 is that it can be used for modifying any sprayer bottle 10 since there is no need to couple the connector 222 to the threaded opening 10D of the sprayer bottle; rather, the connector 222 is simply installed into the sprayer bottle sidewall 10F.

It should be noted that the use of DC power plug 228C/connector 222 is simply by way of example and that it is within the broadest scope of the invention 220 to include all types of electrical connectors for powering the ozonator element 24 and controlling its energization.

As with the insert 20, it is also within the broadest scope of the alternative apparatus 220 to include a user interface with the controller 28A that would permit the user to adjust the AP based on the purity of the water being used in the sprayer bottle 10, as well as being able to adjust the EUP to ensure that ozonated water is always present in the sprayer bottle 10.

It is also within the broadest scope of the alternative apparatus 220 to provide an alternative use of the ozonated water within the sprayer bottle: a potable water source, especially in emergencies. The ozonated water in the sprayer bottle 10 can also act as potable water, in addition to the primary use of the ozonated water as cleaning agent.

Figure 12:
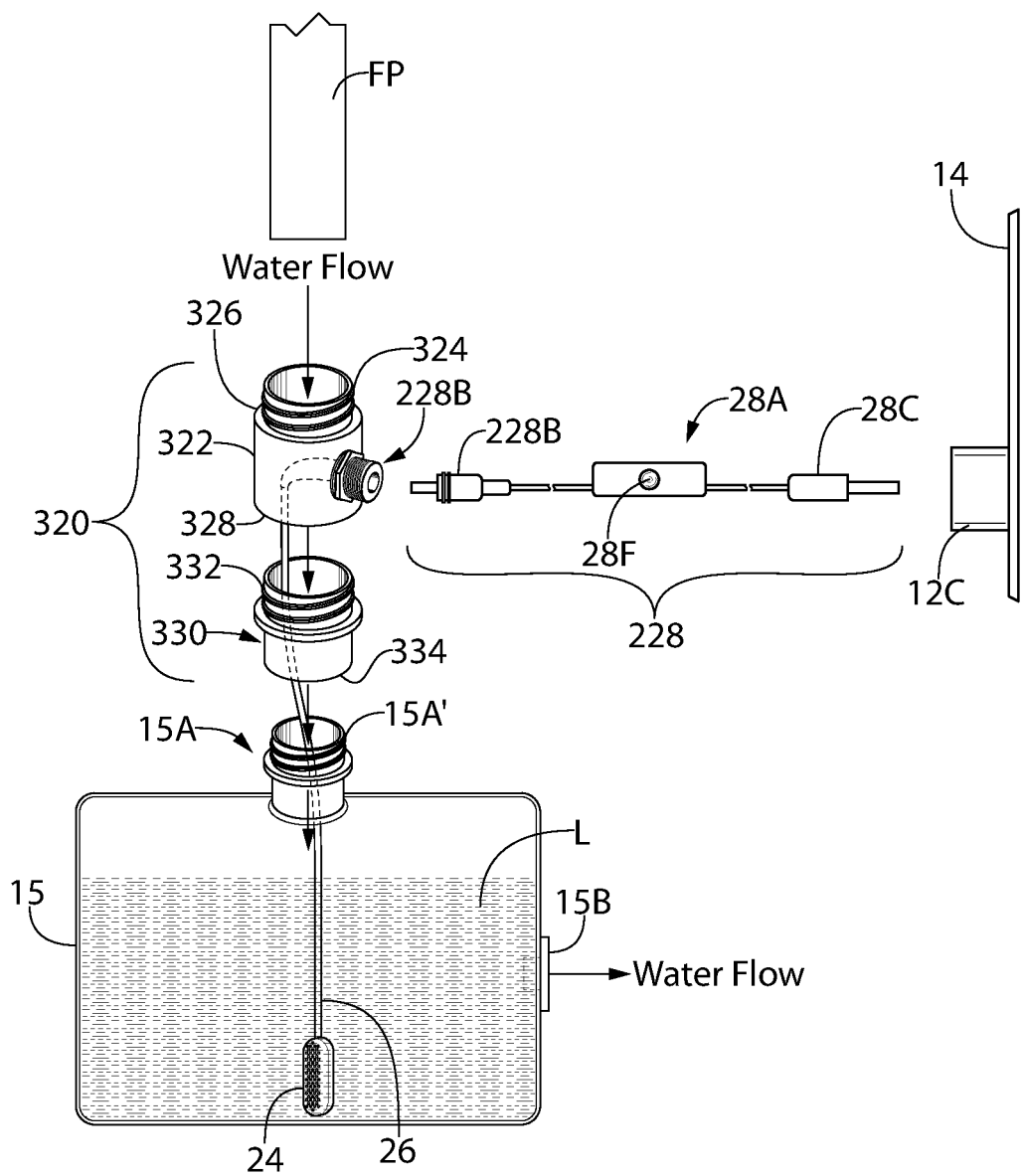

FIG. 12 depicts a variation of the insert 22 for use with water reservoirs (e.g., tanks, accumulators, etc.) to make them ozonating water reservoirs. This can be especially useful for establishing potable drinking water sources quickly where critical drinking water needs arise, such as natural disasters (e.g., hurricanes, tornados, earthquakes, extreme temperature changes, etc.) or other emergencies. A conventional water reservoir 15 comprises an input 15A, for receiving water from a water source (not shown) and an output 15B, for delivering water to a process (also not shown), e.g., a potable water source, a cleaning station, etc. A feedpipe FP to the reservoir 15 may comprise a female coupling that couples to the reservoir's input 15A, e.g., a male threaded connector.

To modify the water reservoir into an ozonating water reservoir, an inventive coupler 320 is provided, as shown in FIG. 12. The coupler 320 comprises a hollow housing 322 in which the electrical connector 222 is installed, as discussed previously with regard to the alternative apparatus 220. The hollow housing 322 comprises a male threaded portion 324 (e.g., 45/400 male thread) on a first end 326 that couples to the feedpipe FP, and further comprises a second end 328, opposite the first end 326, which includes an internal female threaded portion (e.g., 45/400 female thread). The internal female threaded portion of the housing 322 connects to a hollow adapter 330 via upper male threads 332 on the adapter 330. The adapter 330 includes a lower end 334 that includes an internal female threaded portion for coupling to the male threaded portion 15A' of the reservoir input 15A.

Use of the inventive coupler 320 is as follows. The feedpipe FP is disconnected from the reservoir input 15A. The user has two options for configuring the water reservoir 15 to become an ozonating water reservoir.

The first option has the user connecting the adapter 330 to the reservoir input 15A, feeding the ozonating element 24/electrical cable 26 through the adapter 330 and then down into the water reservoir 15, then connecting the housing 322 to the top of the adapter 330 and then connecting the feedpipe FP to the top of the housing 332.

The second option has the user first feed the ozonating element 24/electrical cable 26 through the adapter 330 and then connecting the adapter 330 to the bottom of the housing 322. The user then feeds the ozonating element 24/electrical cable 26 down through the reservoir input 15A and into reservoir 15. Next, the user then connects the lower end 334 of the adapter 330 to the reservoir input 15A. The user completes the process by connecting the feedpipe FP to the top of the housing 322.

The inventive coupler 320 is now ready to be activated by connecting the DC power plug 228C to the connector 222 via the power cord 228. Operation of the inventive coupler 320 to have the water reservoir 15 generate a source of ozonated water is similar to the previous discussion for FIGS. 5 and 11. However, since the water reservoir 15 is typically always connected to the feedpipe FP, the reservoir 15 is thus usually filled with water; as such, steps 202' 204, 206' and 208' of FIG. 11 are not required. If, on the other hand, the water reservoir 15 is portable, then those steps of FIG. 11 apply.

Moreover, it should be understood that in view of the foregoing, different adapters 330 having respective internal female threads on the lower end 334 of the adapter 330 may be provided for coupling to differently sized water reservoir input connectors 15A.

It should be noted that the use of DC power plug 228C/connector 222 is simply by way of example and that it is within the broadest scope of the invention 220 to include all types of electrical connectors for powering the ozonator element 24 and controlling its energization.

As with the insert 20/alternative apparatus 220, it is also within the broadest scope of the inventive coupler 320 to include a user interface with the controller 28A that would permit the user to adjust the AP based on the purity of the water being used in the water reservoir 15, as well as being able to adjust the EUP to ensure that ozonated water is always present in the water reservoir 15. The ability to adjust the AP and EUP is also important depending of the size of the water reservoir 15 where the volume of water therein may require that the AP and EUP be adjusted accordingly.

Because the inventive coupler 320 allows a water reservoir 15 to ozonate the water therein, the ozonated water therein can be used as potable water or as a cleaning agent, as discussed previously with the regard to the insert 20 and the alternative apparatus 220.

Ionized Water Feature in Addition to the Ozonated Water Feature

Figure 20:
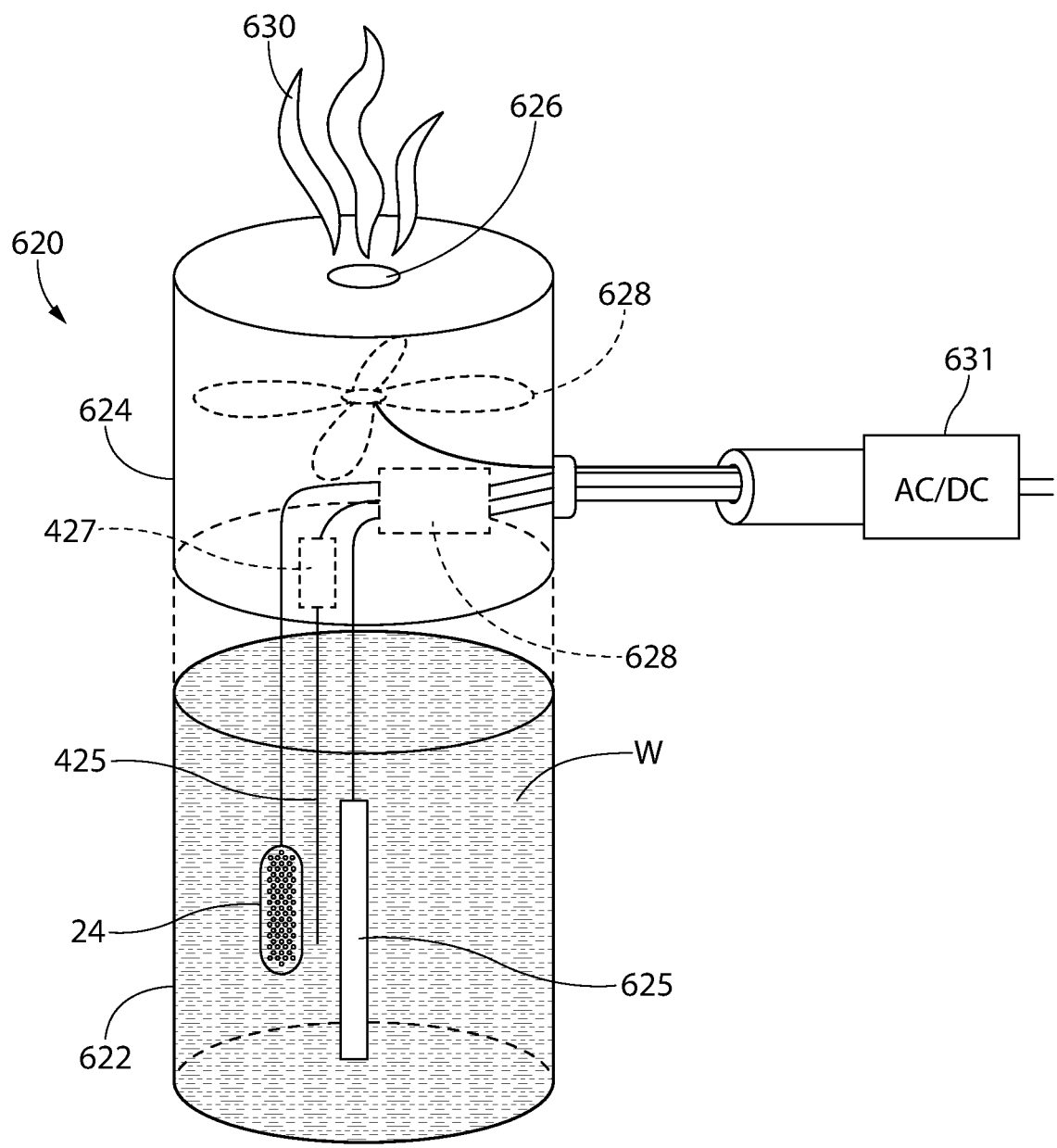
Figure 21:
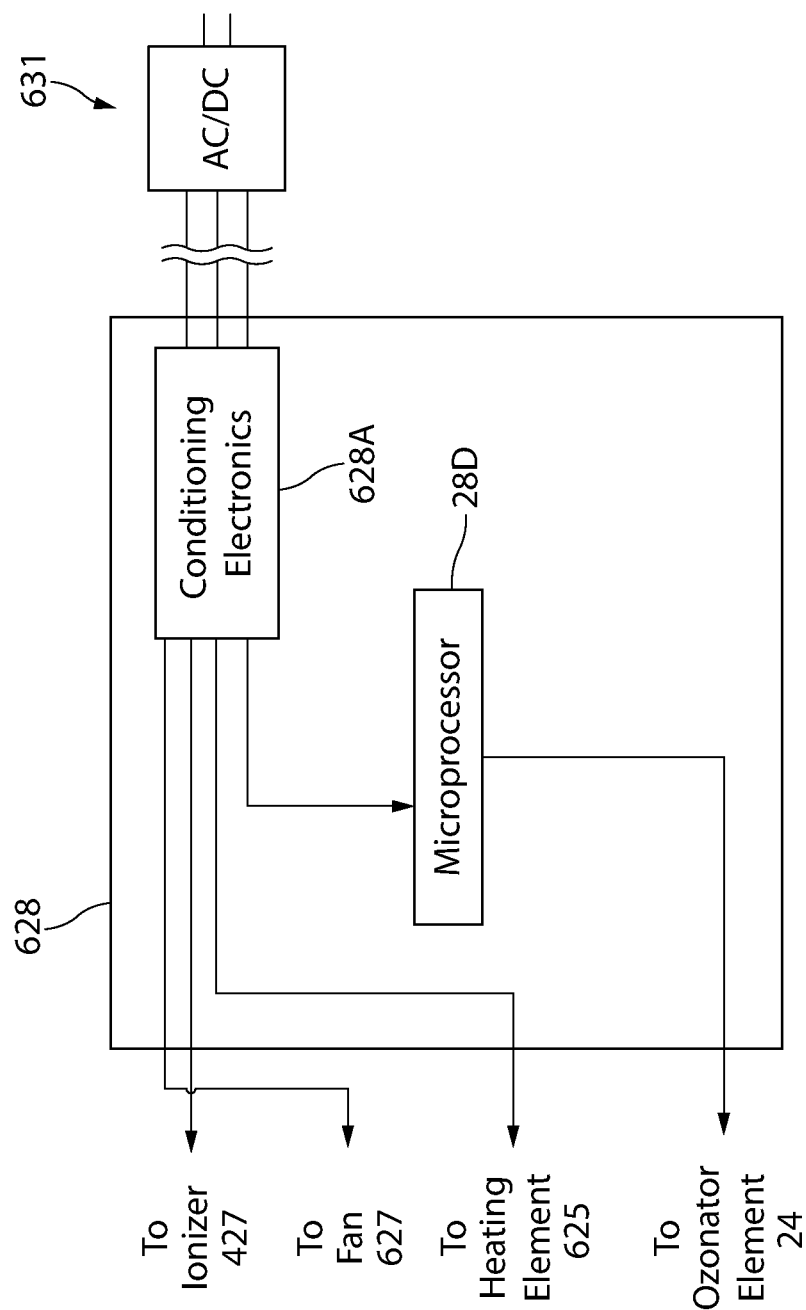
Figure 22:
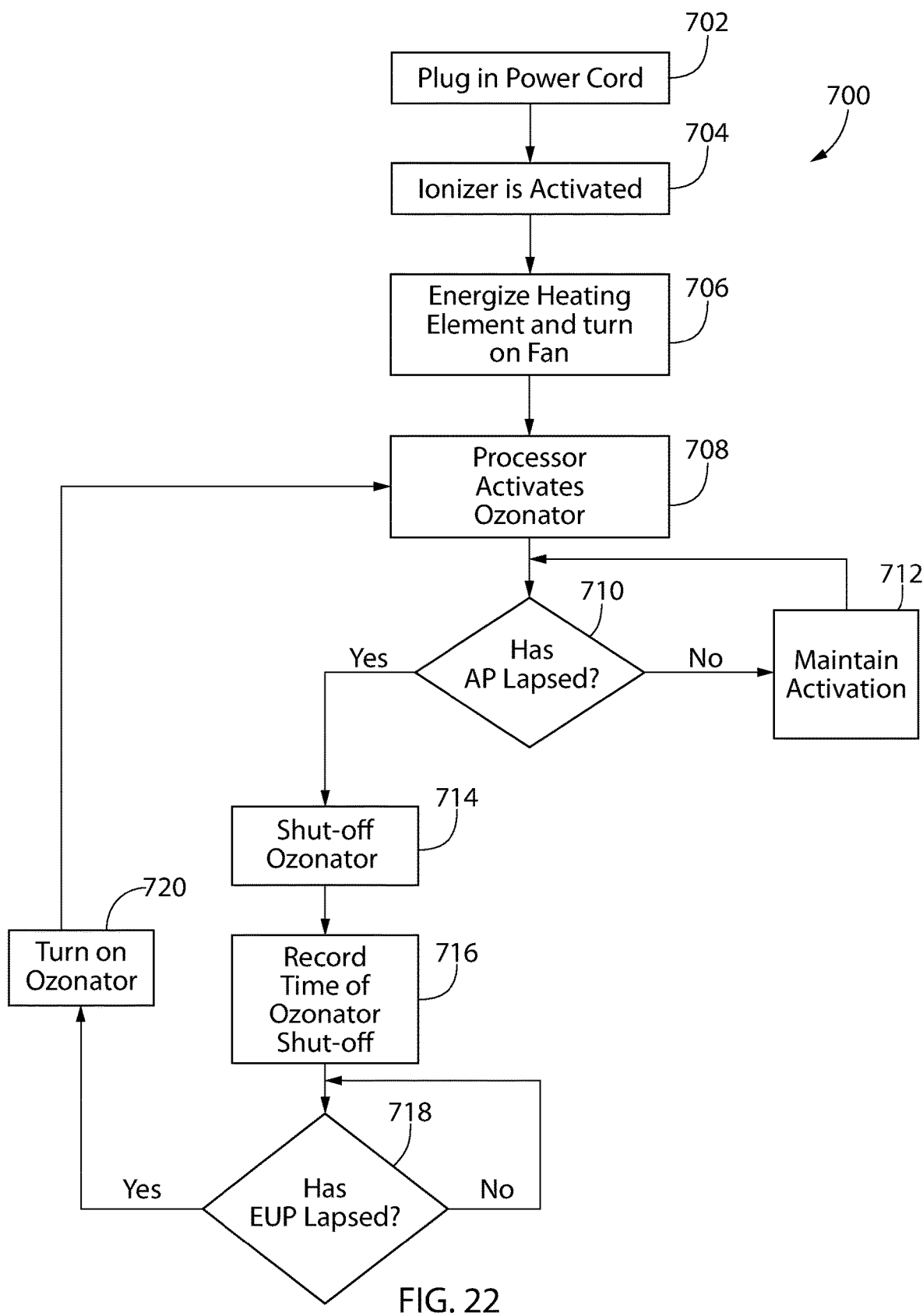

As mentioned previously, it is within the broadest scope of the invention to provide an ionized water aspect to the aforementioned inventive devices. FIGS. 13-19 depict examples of such devices providing an ozonated/ionized water (OIW) cleaning fluid. Moreover, FIGS. 20-22 are directed to a novel humidifier or vaporizer device that provides an OIW mist or vapor.

Providing an ionized water mist into the air causes airborne viruses, bacteria or mold to "clump" together around the ionized water molecules and, as a result, fall out of the air. This is especially important in reducing airborne diseases, such as COVID-19, and other undesirable airborne particles.

Figure 13:
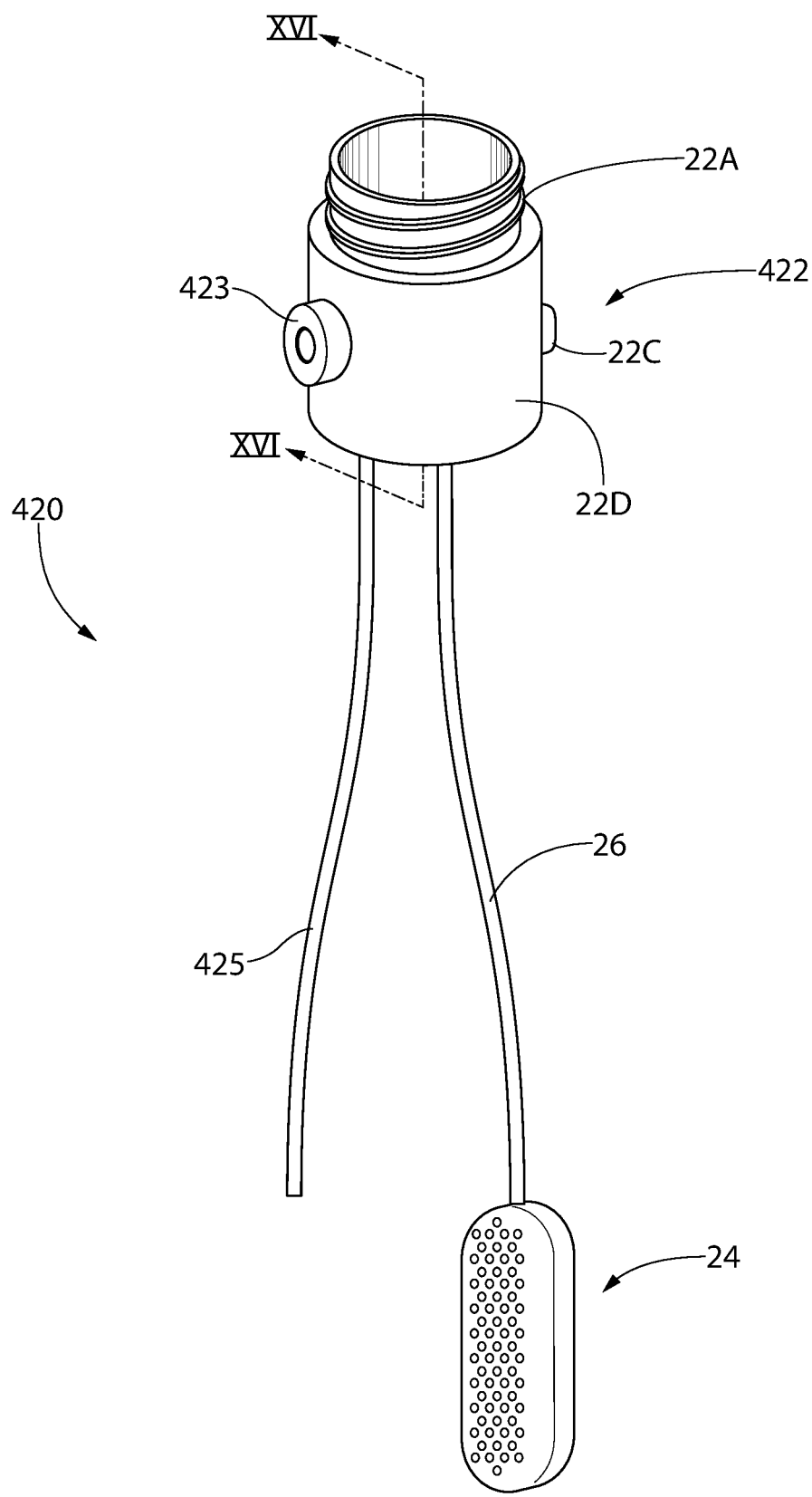
Figure 14:
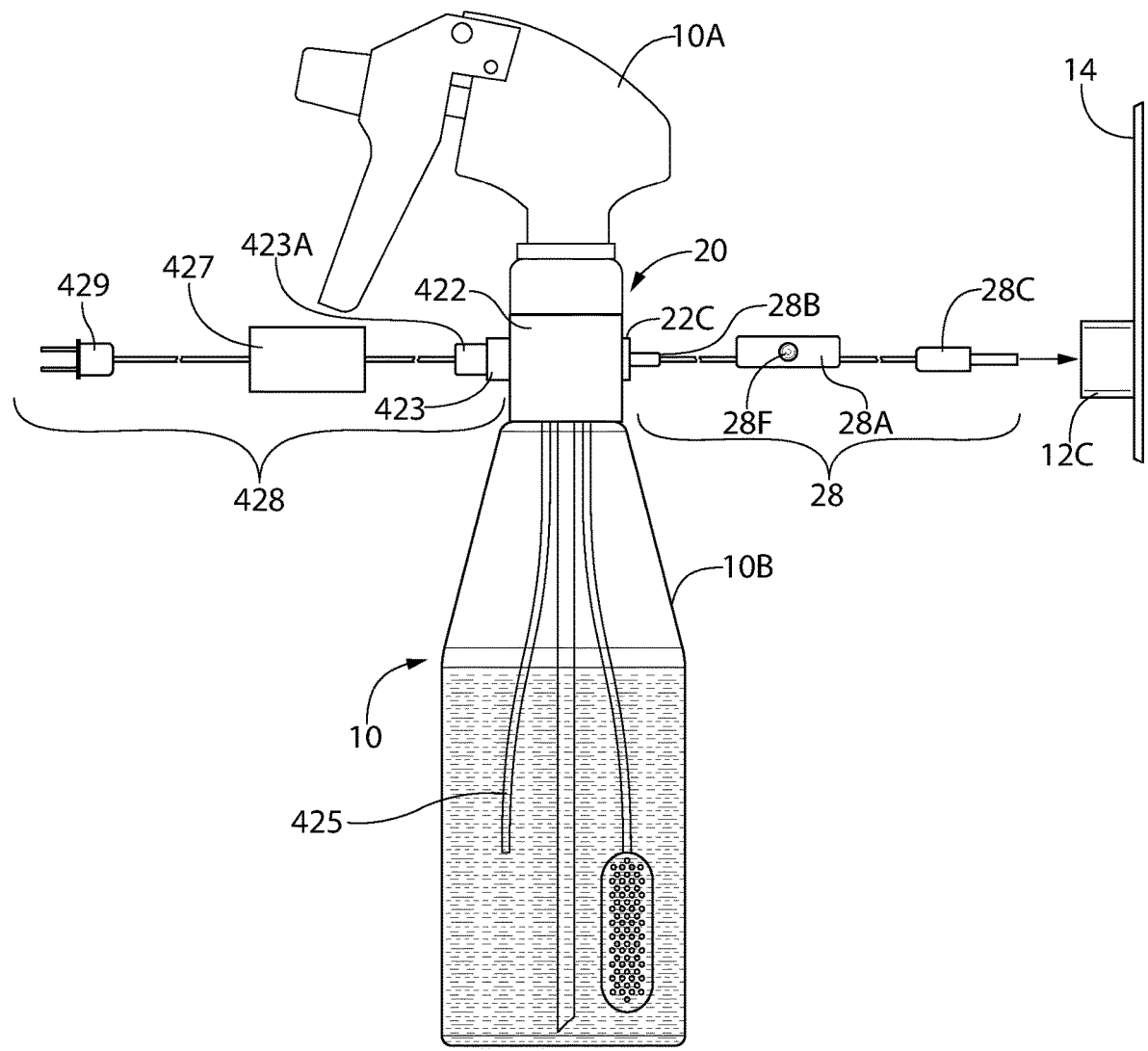
Figure 15:
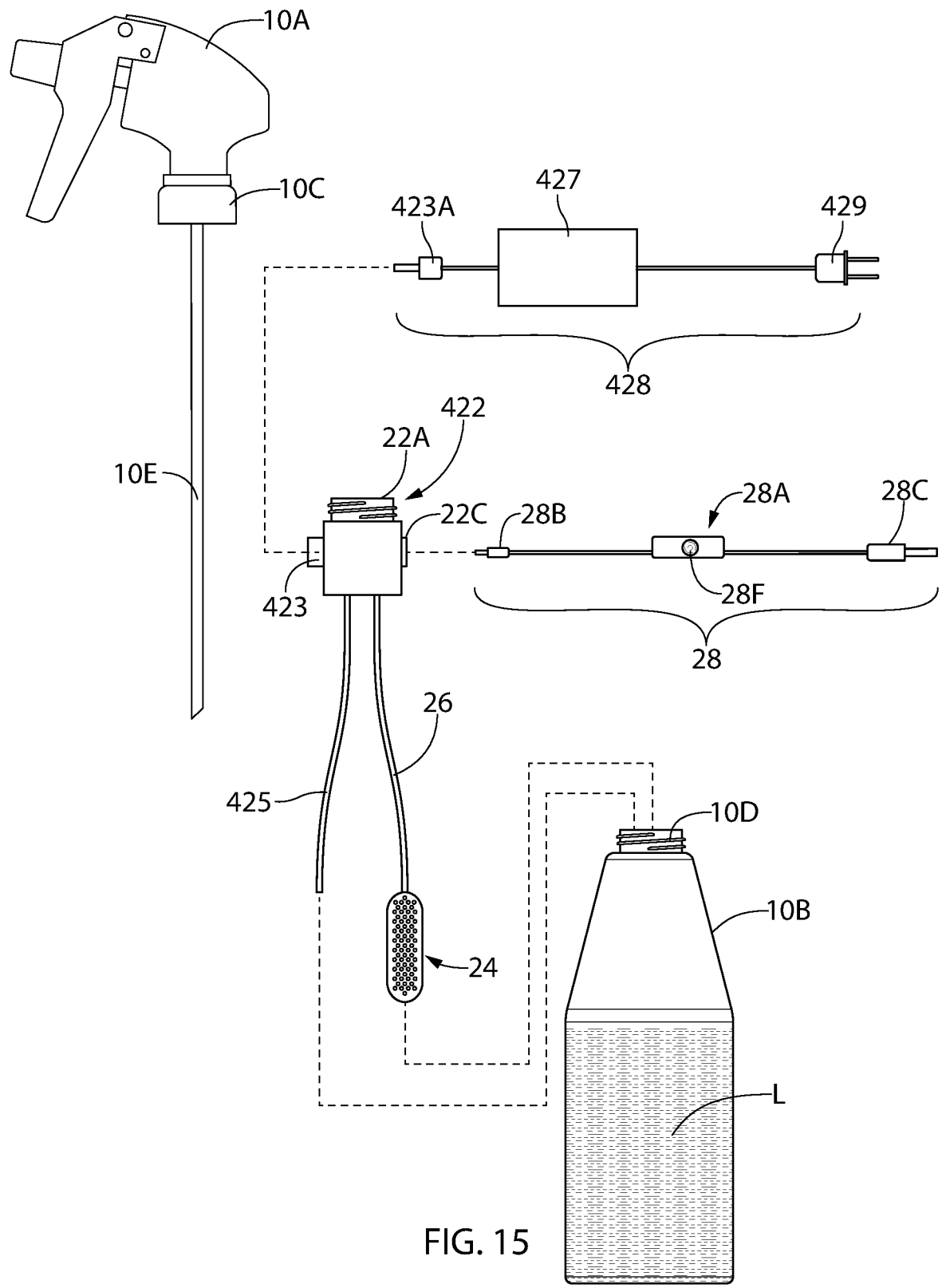

To that end, as shown in FIGS. 13-16 (corresponding to FIGS. 1-4) depict a modified version 420 of the insert assembly 20 that includes a provision for ionizing the water in the bottle also. In particular, FIG. 13 depicts the insert assembly 420 of the present invention which comprises an insert member 422 which is similar in every aspect to the insert assembly 20 but also comprises an electrical connector 423 (e.g., a USB receptacle) in the sidewall 22D. As shown most clearly in FIG. 16, the internal side 423B of the electrical connector 423 is fixedly connected to a first end of an ionizer electrical lead 425 (hereinafter the "ionizer lead"). The other end of the ionizer lead 425 is free and is configured for placement within the water to be ionized.

A distinct power cord 428 (see FIGS. 14-15) is provided for energizing the ionizer lead 425. In particular, the power cord 428 comprises an ionizer 427 (e.g., a commercially-available ionizer may comprise the negative ion generator purifier black ionizer generator module for DC5V<1 W US, available on eBay, etc.) having the electrical connector 423 on its output side and comprising, on its input side, a power connector 429 on its other end for connecting to utility power via an AC/DC converter (not shown which may be a part of the ionizer 427 itself).

It should be noted that the electrical connector 423 is different from the electrical connector 22C to prevent the inadvertent connection of the ozonator cable 28 into the ionizer plug 423 and vice versa.

Unlike the ozonator element 24, the ionizer lead 425 does not require any timing limitations and once powered, it begins ionizing the water, in which it is positioned, immediately. As such, the ionizer lead 425 can operate independently of the ozonating element. Thus, the flow diagrams of FIG. 5-5A discussed previously with the insert assembly 20, are still applicable for the insert assembly 420.

Figure 16:
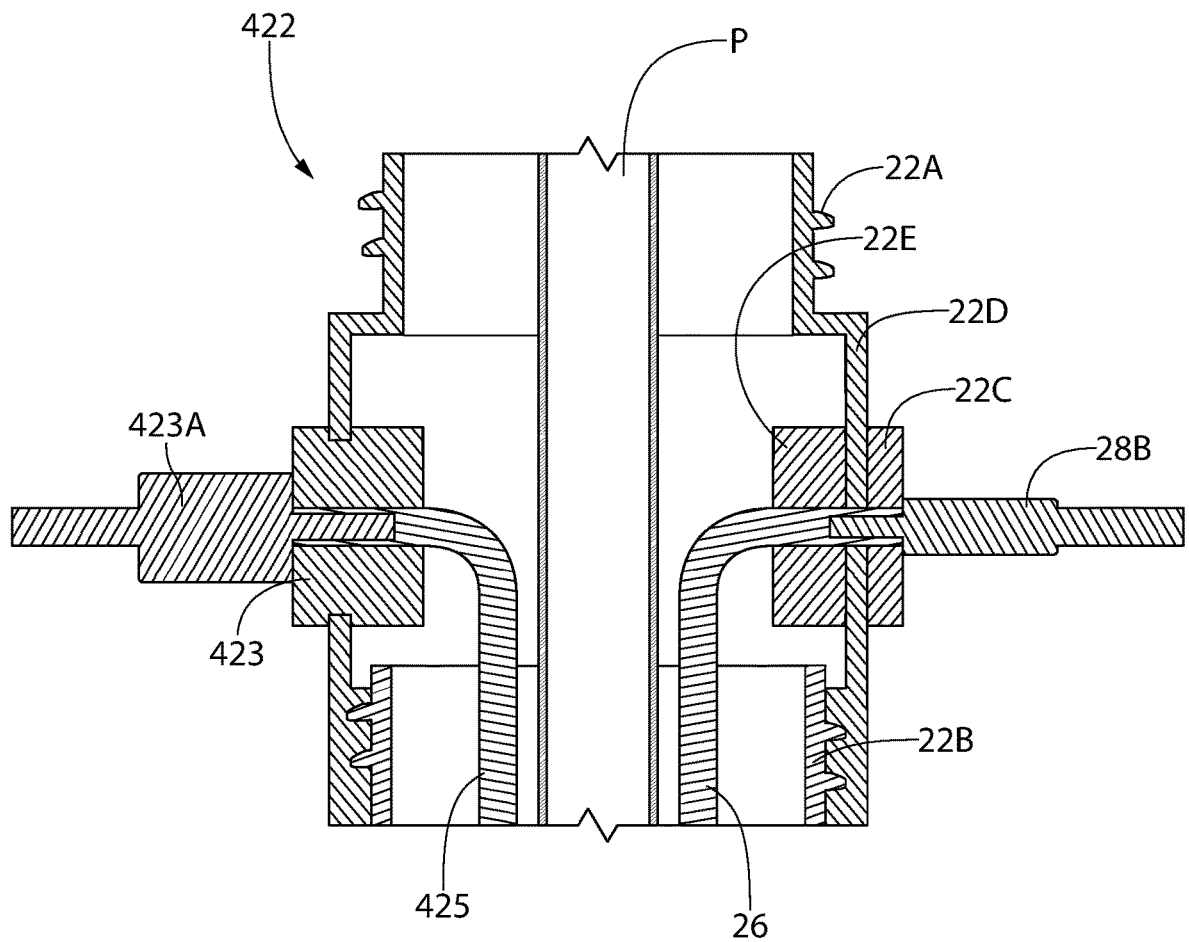

It should be further noted that, as shown in FIG. 16, the presence of the ionizer lead 425 does not obstruct the passageway P in the insert assembly 420 and thus the spray head dip tube 10E can easily be inserted or removed through the passageway P.

Figure 17:
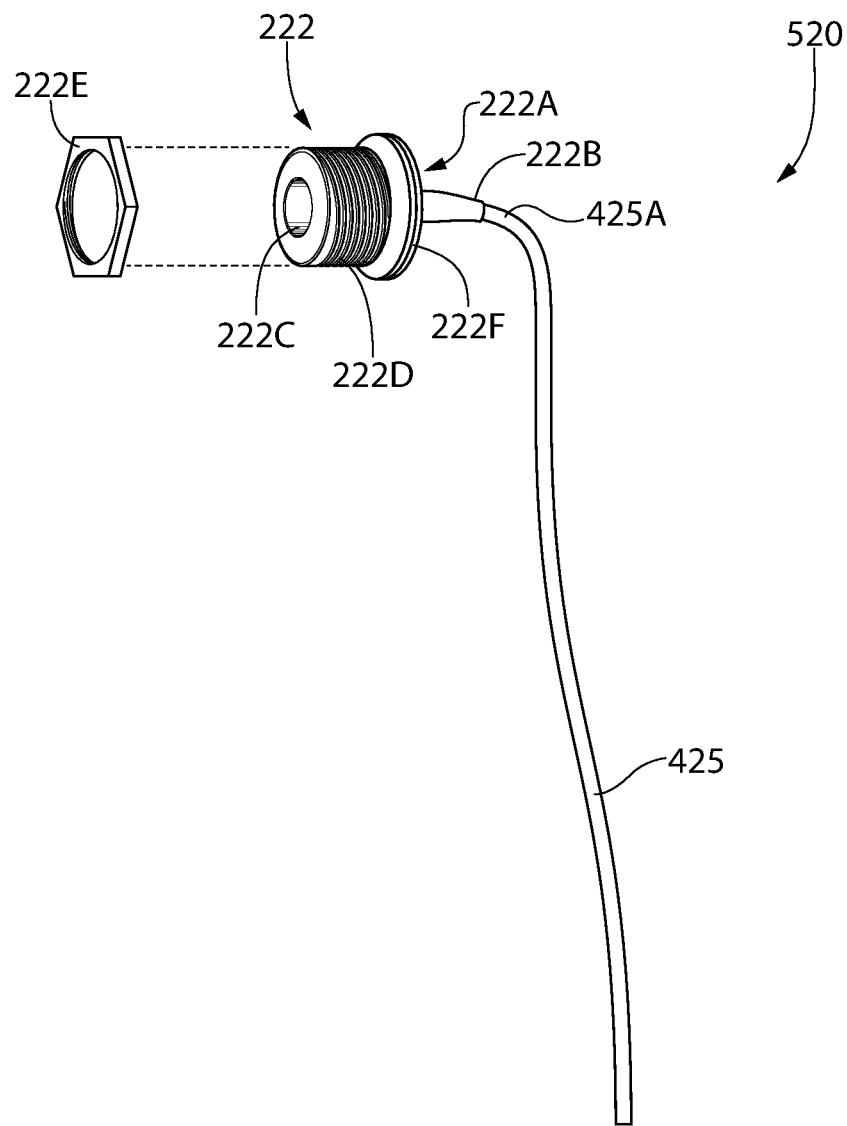
Figure 18:
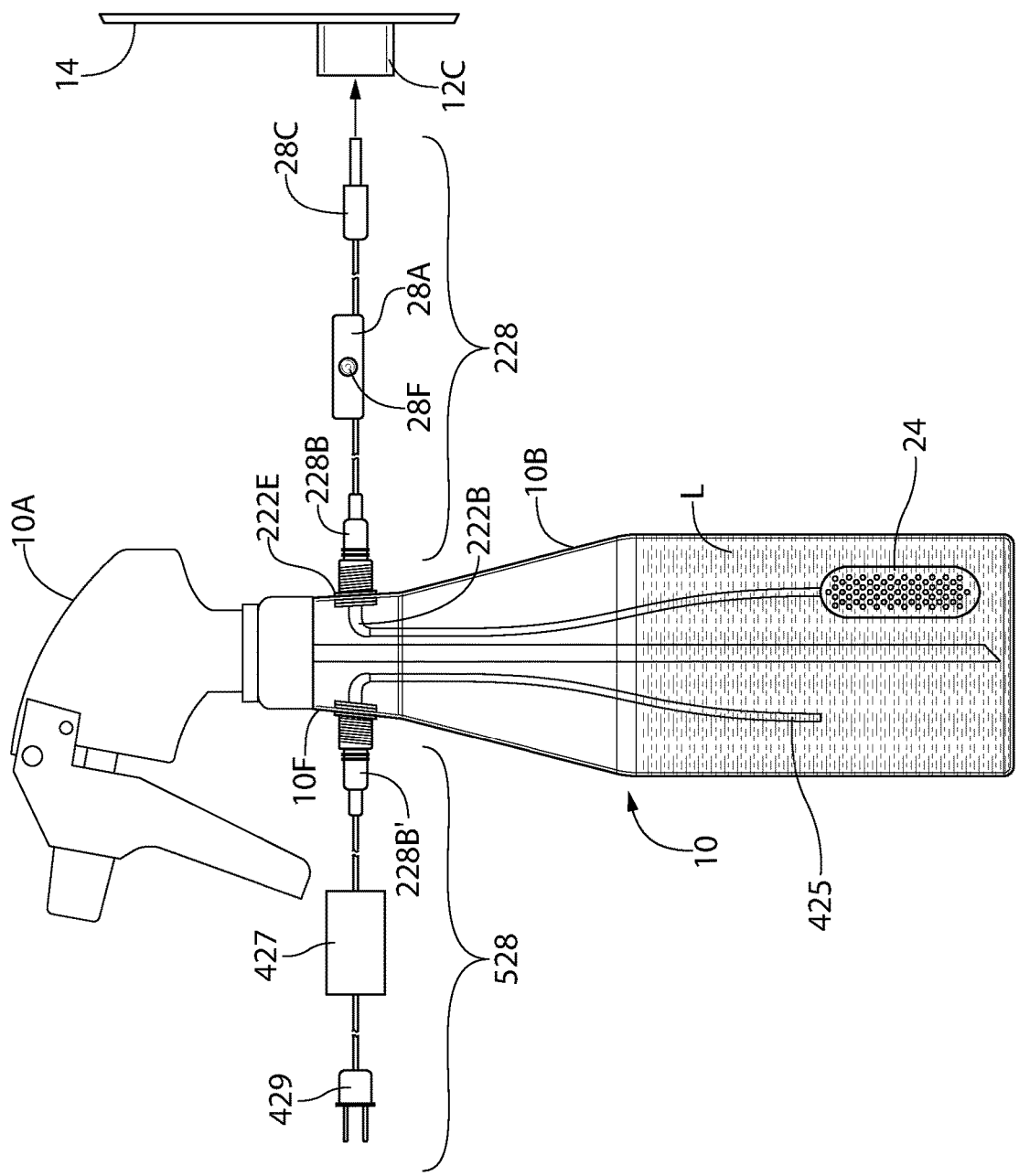
Figure 19:
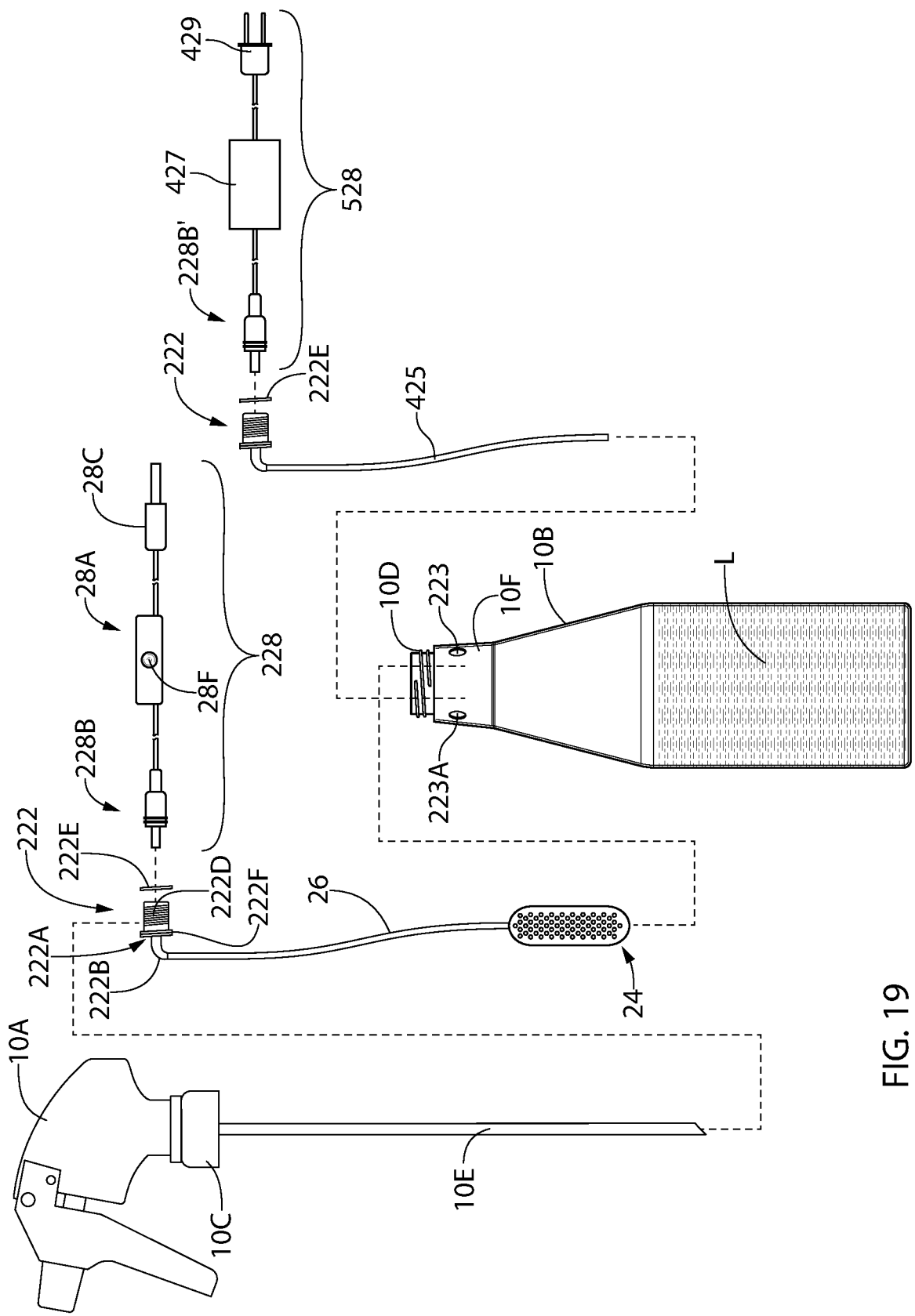

FIGS. 17-19 (corresponding to FIGS. 8-10) depict a modified version 520 of the alternative apparatus 220 that also includes a provision for ionizing the water in the bottle. In particular, FIG. 17 shows that in alternative apparatus 520, the ionizer lead 425 has its own electrical connector 222 coupled to the upper end of the ionizer lead 425 which is installed in the wall itself of the bottle portion 10B, through a hole 223A drilled through the sidewall 10F of the sprayer bottle 10. As with the alternative apparatus 220, in the alternative apparatus 520, the other end 425A of the ionizer lead 425 is coupled (e.g., soldered) to one side 222A of the electrical connector 222 which is then covered with a shrink wrap 222B. The opposite side of the connector 222 comprises the electrical receptacle 222C surrounded by the screw thread 222D having the corresponding nut 222E. The shoulder 222F provides the flange against which the connector 222 is able to seat against the internal wall of the bottle portion 10B, as described above with regard to the alternative apparatus 220 and is not repeated here.

The power cord 528 for the ionizer lead 425 is similar to the power cord 428 except that the instead of having the electrical connector 423A on one end, the power cord 528 includes the electrical connector 228B' on that end, which was discussed earlier with regard to alternative apparatus 220 and is not repeated here. It should be noted that connector 228B of cable 228 and 228B' of cable differ in that a keying element (not shown) which is present on 228B' that prevents it from being inadvertently inserted into connector 222 for the ozonator element 24 and, as such, the connector 228B' can only be inserted into the connector 222 that connects to the ionizer lead 425. Furthermore, the flow diagrams of FIG. 5-5A discussed previously with the insert assembly 20, are still applicable for the second embodiment 520 of the alternative apparatus.

As with the second embodiment of the insert assembly 420, the presence of the ionizer lead 425 coupled to the bottle sidewall 10F, along with the ozonator element conductor 26 also coupled to the sidewall 10F, does not obstruct a passageway through the top of the bottle 10 and thus the spray head dip tube 10E can easily be inserted or removed through that opening.

It should be understood that in view of the foregoing, the inventive coupler 320 of FIG. 12 can also be modified in accordance with the previous discussion with regard to FIGS. 17-19 to provide an ozonated and ionized water product for use in the water reservoir 15 as well.

FIGS. 20-22 depict a novel humidifying or vaporizing device (HVD) 620 that provides a water vapor mist that is an OIW mist. As shown most clearly in FIG. 20, the device 620 may comprise a lower water reservoir portion 622 for holding a volume of water. An upper removable portion 624 comprises the electronics for the HVD 620 and from which the ozonator element 24 and the ionizer lead 425 project downward so as to be submerged in the water W contained in the reservoir portion 622. In addition, when the HVD 620 acts as a vaporizer, an energizing element 625 is provided. The energizing element 625 (hereinafter "element 625") may comprise a heating element (e.g., ceramic heater, etc.) or an ultrasonic vaporizing element (e.g., WDHTS 20 mm 113 kHz ultrasonic atomization maker mist Atomizer) or any other element used for converting the ozonated/ionized water into the OIW mist or vapor 630 and also projects downward from the upper portion 624 so it too can be submerged in the water W.

The HVD 620 provides an OIW mist 630 through an opening 626 in the upper portion 624, A fan 627 blows the OIW mist 630 up through the opening 626. As shown in FIG. 21, the electronics 628 comprises conditioning electronics 628A that provides the proper voltage/current from the utility power, via a plug/AC-DC converter 631 to energize the previously-mentioned components. It should be noted that the ionizer 427 (FIG. 20) is also located within the upper portion 624, rather than being present in the power cord, as discussed previously. Since generating ozonated water has time limitations, described previously, the ozonater element 24 is controlled by the microprocessor 28D as mentioned previously with regard to FIG. 5. As such, a modified flow diagram of FIG. 5 is provided in FIG. 22 to exemplify the HWD 620 and microprocessor 28D operation 700. In particular, the upper portion 624 is removed by the user from the lower portion 622. Water is poured into the lower portion 622 and the upper portion 624 is then restored on top of the lower portion 622, thereby submerging the ionizer lead 425, the ozonater element 24 and the element 625. At that point, the user plugs in the power cord at step 702 which then energizes the ionizer 427/ionizer lead 425 for generating the ionized water state in step 704, as well as turning on the element 625 and fan in step 706. The processor 28D then activates the ozonator element 24 at step 708 for the activation period (AP) discussed previously in FIG. 5. At step 710, the processor 28D monitors the time to determine if the AP has been met or not (step 712). If the AP has been met, at step 714 the processor 28D shuts off the ozonator element 24. At step 716, the processor 28D records the time when the ozonator element 24 was shut off then monitors, at step 718, whether the effective use period (EUP, discussed above with regard to FIG. 5) has lapsed or not. If it has, then at step 720, the processor turns on the ozonator element 24 and returns to step 708 to begin the process of generating a new OIW mist 630.

Figure 23:
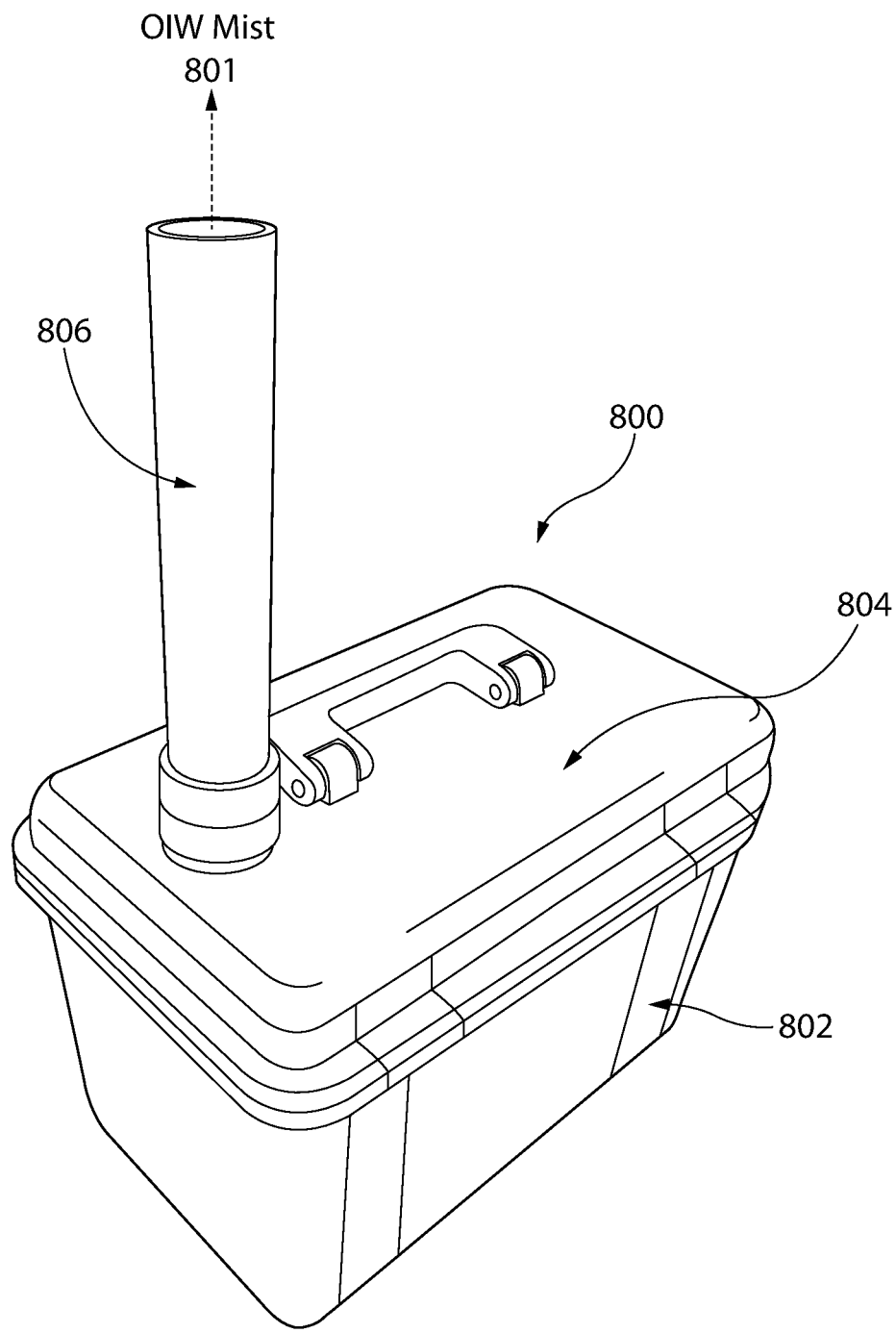
Figure 24:
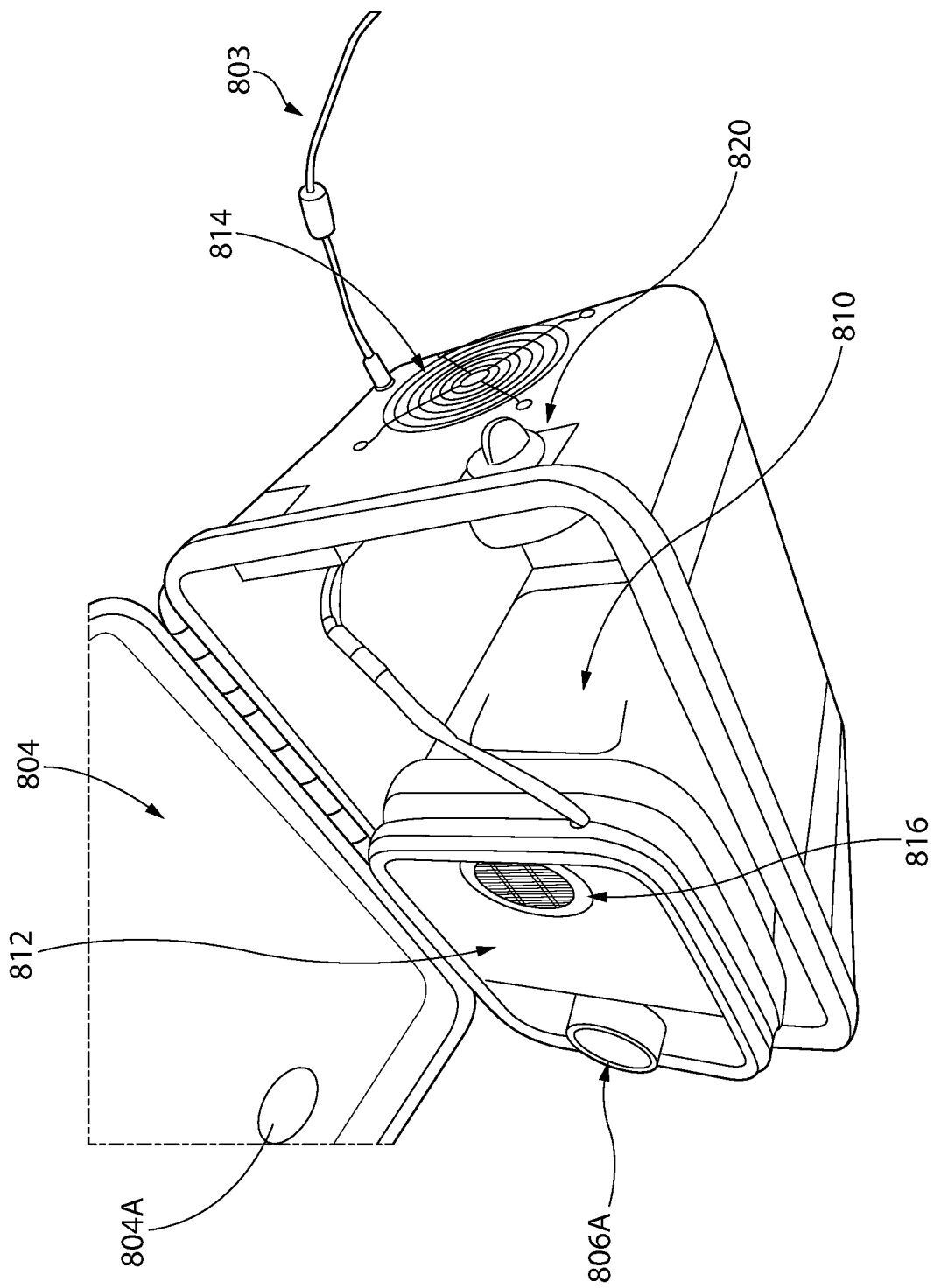
Figure 24A:
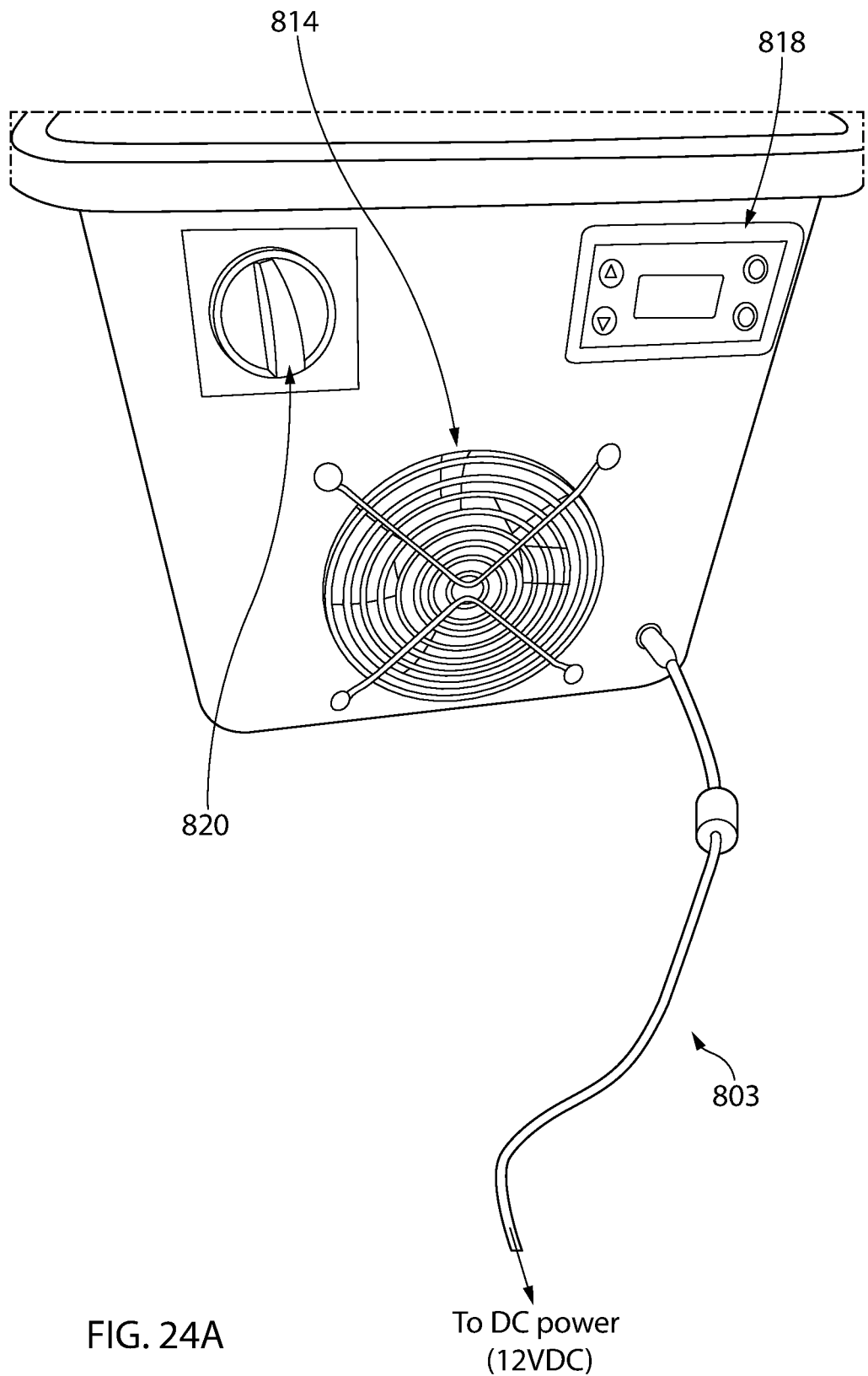
Figure 25:
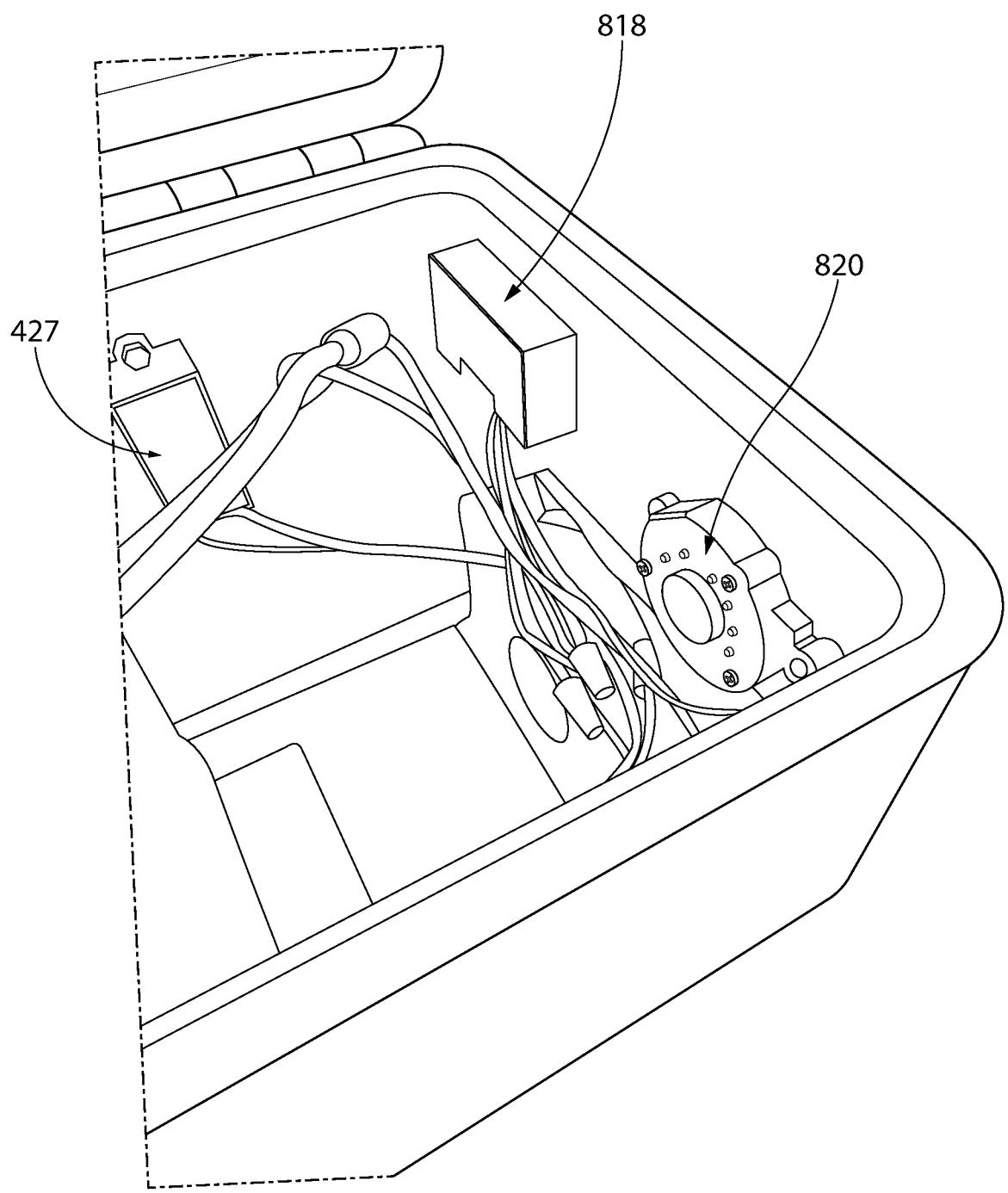
Figure 26:
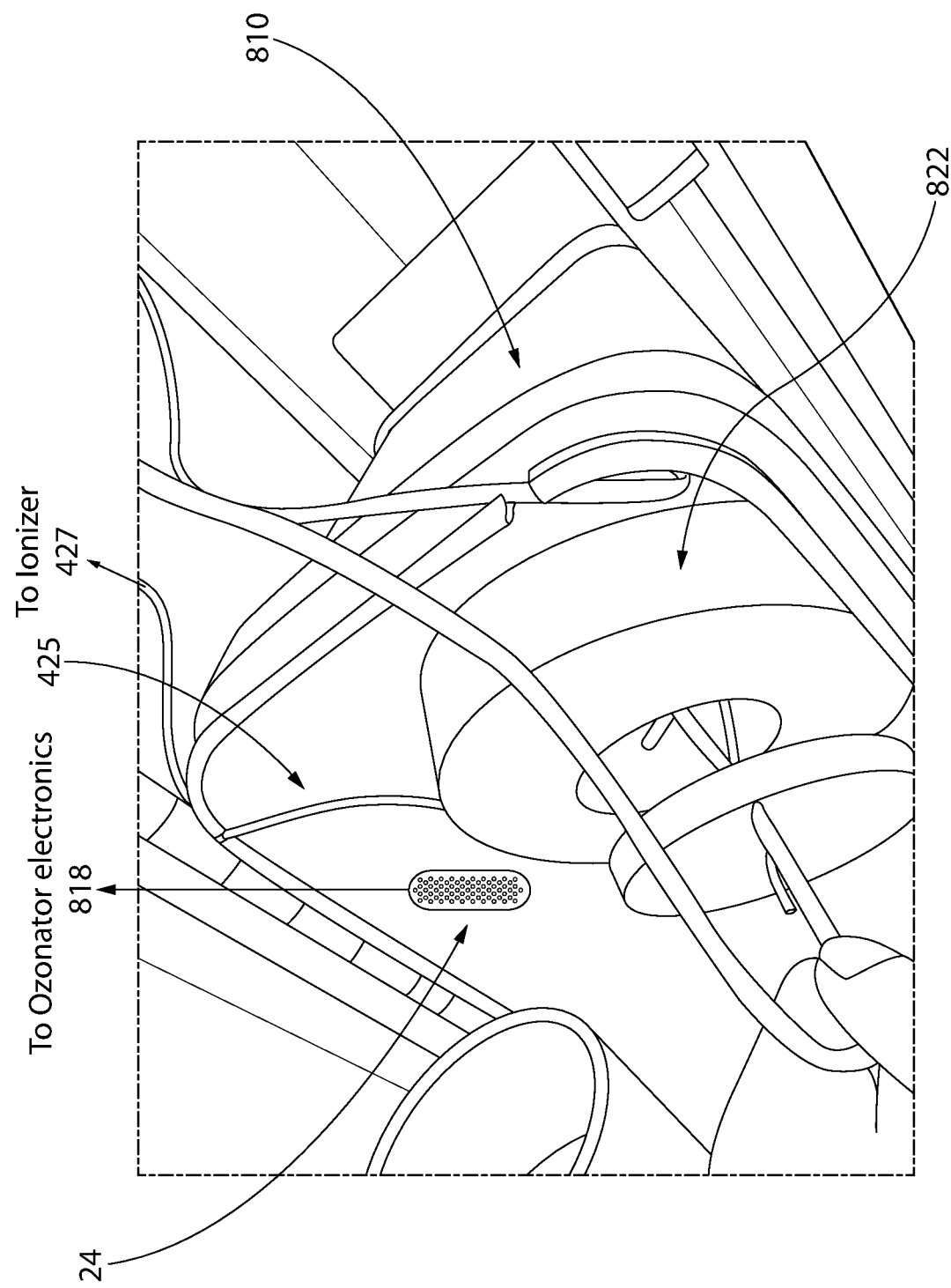

FIGS. 23-27 depict an embodiment of a device for providing another portable misting/cleaning tool 800, hereinafter "device 800" for generating an OIW mist 801. As shown in FIG. 23, the device 800 is contained within a portable carrier 802 having a lid 804 that has the appearance of a "tool box". When the lid 804 is opened, as shown most clearly in FIG. 24, a container 810 is disposed therein. The container 810 has a lid 812 and is filled with water and into which is positioned the ozonating element 24 (FIG. 26), the ionizer lead 425 and an energizing element 822 (e.g., an ultrasonic humidifier, ceramic heater, etc.) which corresponds to the energizing element 625 of the HVD 620 of FIGS. 20-22; the ozonator element 24 is coupled to ozonator electronics 818 that control its operation as discussed previously. The portable carrier 802 comprises a fan 814 (FIGS. 24-24A) that pulls air into the interior of the carrier 802 and into an air intake 816 in the container lid 812. The ozonator electronics 818 and the ionizer 427 are mounted inside the portable carrier 802, as shown most clearly in FIG. 25. Timer electronics 820 are provided on the portable carrier 802 to allow the operator to set the overall operation of the device 800. Power is provided to all of the electronics via a power cable 803 configured to a DC power module for coupling to vehicle power, e.g., 12 VDC, by way of example only.

Figure 27:
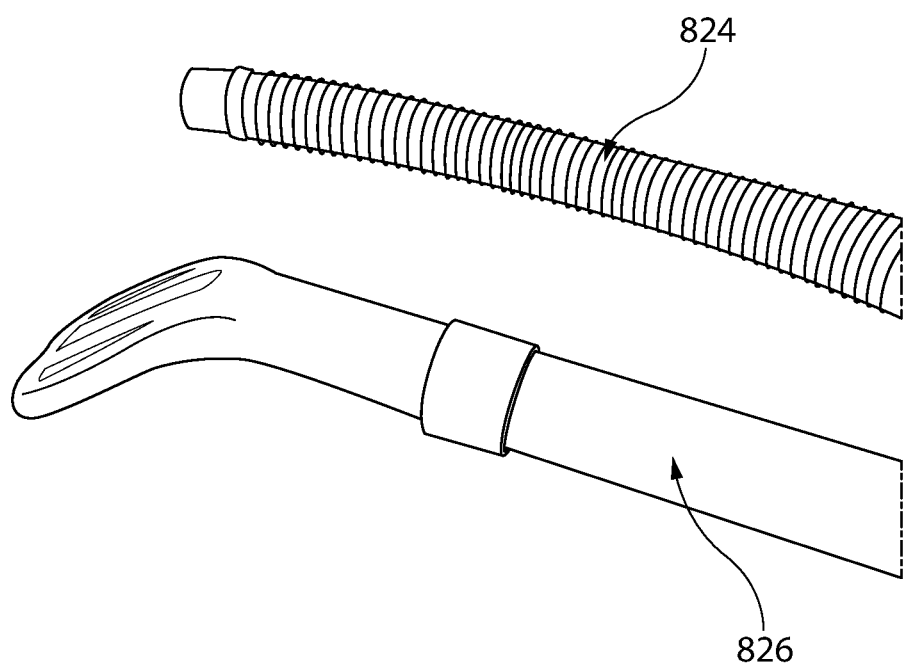

When it is desired to have the device 800 operate as an OIW mist 801 generator for the environment, the operator can couple an output pipe 806 (FIG. 24) down through an aperture 804A in the carrier lid 804 and into engagement with a collar 806A in the container lid 812. If, on the other hand, the operator wishes to use the OIW mist 801 for cleaning a particular item or vicinity, the operator can disengage the pipe 806 and connect other accessories to the collar 806A, such as the flexible tube 824 (FIG. 27) or the rigid cleaning wand 826 (FIG. 27).

While the invention has been described in detail and with reference to specific examples thereof, it will be apparent to one skilled in the art that various changes and modifications can be made therein without departing from the spirit and scope thereof.

What is claimed is:

1. An apparatus for permitting a conventional spray bottle to generate ozonated and ionized water, the conventional spray bottle having a spray head and bottle portion, said apparatus comprising:

first and second electrical connectors associated with the bottle portion;

an ozonator element that is coupled to said first electrical connector via an electrical cable and wherein said ozonator element is configured to be submerged within water contained within the bottle portion;

an ionizer lead that is coupled to the second electrical connector and wherein said ionizer lead is configured to be submerged within the water contained in the bottle portion;

wherein said first electrical connector conveys electrical power to said ozonator element to activate said ozonator element to ozonate the water contained in the bottle portion and wherein an ionizer is also coupled to said second electrical connector for energizing said ionizer lead to ionize the water contained in the bottle portion.

2. The apparatus of claim 1 comprising an insert member that can be releasably inserted between the spray head and the bottle portion, said first and second electrical connectors being positioned within a wall of said insert member.

3. The apparatus of claim 2 wherein said insert comprises a first threaded portion for releasably securing to the spray head and a second threaded portion for releasably securing to a top portion of the bottle portion.

4. The apparatus of claim 2 wherein said insert comprises an internal volume that permits a dip tube of the spray head to pass therethrough along with the electrical cable and said ionizer lead.

5. The apparatus of claim 2 wherein said first electrical connector is configured for receiving a power cord from an external power source for providing the electrical power to said ozonator element and said ionizer is coupled to another external power source for energizing said ionizer.

6. The apparatus of claim 1 wherein said ozonated and ionized water contained within the bottle portion is used as a cleaning agent.

7. The apparatus of claim 1 wherein said first and second electrical connectors are positioned in respective apertures in a sidewall of the bottle portion, each of said electrical connectors comprising a threaded portion with a shoulder and a corresponding nut, said shoulder being positioned against an internal side of the sidewall with said threaded portion protruding outward from the sidewall and wherein said nut is threadedly engaged with said threaded portion and in contact with an external side of the sidewall for releasably securing said electrical connectors to the sidewall.

8. The apparatus of claim 7 wherein said first electrical connector is configured for receiving a power cord from an external power source for providing the electrical power to said ozonator element and wherein said ionizer is coupled to another external power source for energizing said ionizer.

9. An apparatus for generating an ozonated and ionized water mist or vapor, said apparatus comprising:

a housing configured to contain water;

an ozonator element that is configured to be submerged within the water and which is coupled to electrical power via a first conductor to ozonate the water in the housing;

an ionizer having an ionizer lead, said ionizer lead being configured to be submerged within the water, and wherein said ionizer is coupled to the electrical power via a second conductor to ionize the water in the housing; and an energizing element that is configured to be submerged within the water and which is coupled to the electrical power via a third conductor for converting the ozonated and ionized water into an ozonated and ionized mist or vapor.

10. The apparatus of claim 9 wherein said energizing element is a heating element.

11. The apparatus of claim 9 wherein said energizing element is an ultrasonic vaporizing element.

12. The apparatus of claim 9 further comprises a fan for forcing the ozonated and ionized water mist or vapor out of an opening in said housing.

13. The apparatus of claim 9 further comprising a carrier into which said housing is positioned, said carrier comprising an electrical interface for permitting said apparatus to be connected to vehicle power.

14. The apparatus of claim 13 wherein said housing comprises a collar for permitting cleaning accessories to be coupled thereto.

15. The apparatus of claim 14 wherein said cleaning accessory comprises a flexible tubing.

16. The apparatus of claim 14 wherein said cleaning accessory comprises a rigid cleaning wand.

17. A method of ozonating and ionizing water in a conventional spray bottle having a spray head with a dip tube and a bottle portion, said method comprising:

providing an insert member having an internal passageway and wherein said insert member can be releasably inserted between the spray head and the bottle portion, said insert member further comprising an ozonator element that is coupled to said insert member via an electrical cable and an ionizer lead that is electrically coupled to said insert member;

submerging said ozonator element and said ionizer lead within the water contained within the bottle portion;

inserting the dip tube through said insert member and into the bottle portion;

releasably securing a first end of said insert member to an opening in the bottle portion and a second end, opposite said first end, of said insert member to the spray head;

applying electrical power to said insert member to activate said ozonator element to ozonate the water in the bottle portion and to an ionizer that is electrically coupled to said insert and to said ionizer lead to also ionize the water in the bottle portion.

18. The method of claim 17 wherein said step of providing an insert member comprises forming a first threaded portion on said first end for releasably securing to the spray head and a forming second threaded portion on said second end for releasably securing to a top portion of the bottle portion.

19. A method of ozonating and ionizing water in a conventional spray bottle having a spray head with a dip tube and a bottle portion having a top opening, said method comprising:

forming two apertures in a sidewall of the bottle portion;

securing a first electrical connector in one of said apertures and to which an ozonator element is electrically connected via a first electrical cable and securing a second electrical connector in the other one of said apertures and to which an ionizer lead is electrically connected;

passing said ozonator element and said ionizer lead through the top opening and into the interior of the bottle portion;

disposing water into the bottle portion through said top opening;

inserting the dip tube through the top opening and into the bottle portion and releasably securing the spray head to the bottle portion; and coupling a first power cord to said first electrical connector to provide electrical power to activate said ozonator element to ozonate the water in the bottle portion and coupling a second power cord, having an ionizer, to said second electrical connector to provide electrical power to activate said ionizer lead to ionize the water in the bottle portion.

20. A method of generating an ozonated and ionized water mist or vapor, said method comprising:

disposing water in a container;

submerging an ozonator element within the water and which is coupled to electrical power via a first conductor to ozonate the water in the container;

submerging an ionizer lead within the water and wherein the ionizer lead is electrically coupled to an ionizer which is coupled to electrical power via a second conductor to ionize the water in the container; and submerging an energizing element within the water and which is coupled to electrical power via a third conductor for converting the ozonated and ionized water into an ozonated and ionized mist or vapor.

21. The method of claim 20 wherein said energizing element is a heating element.

22. The method of claim 20 wherein said energizing element is an ultrasonic vaporizing element.

23. The method of claim 20 further comprising the step of providing a fan in said container for forcing the ozonated and ionized water mist or vapor out of an opening in said container.

* * * * *